(12) United States Patent
Nakazawa et al.

(10) Patent No.: US 12,233,634 B2
(45) Date of Patent: Feb. 25, 2025

(54) POROUS BODY AND MATERIAL FOR MEDICAL USE

(71) Applicants: National University Corporation Tokyo University of Agriculture and Technology, Tokyo (JP); NIPPON MEDICAL SCHOOL FOUNDATION, Tokyo (JP)

(72) Inventors: Yasumoto Nakazawa, Tokyo (JP); Chiemi Sakata, Tokyo (JP); Shuhei Tara, Tokyo (JP); Eri Koyanagi, Tokyo (JP)

(73) Assignees: National University Corporation Tokyo University of Agriculture and Technology, Tokyo (JP); NIPPON MEDICAL SCHOOL FOUNDATION, Tokyo (JP)

( * ) Notice: Subject to any disclaimer, the term of this patent is extended or adjusted under 35 U.S.C. 154(b) by 1115 days.

(21) Appl. No.: 16/972,603

(22) PCT Filed: Jun. 5, 2019

(86) PCT No.: PCT/JP2019/022418
§ 371 (c)(1),
(2) Date: Dec. 6, 2020

(87) PCT Pub. No.: WO2019/235543
PCT Pub. Date: Dec. 12, 2019

(65) Prior Publication Data
US 2021/0299333 A1  Sep. 30, 2021

(30) Foreign Application Priority Data

Jun. 5, 2018 (JP) .................................. 2018-108148

(51) Int. Cl.
*B32B 5/08* (2006.01)
*B32B 5/26* (2006.01)
(Continued)

(52) U.S. Cl.
CPC ................ *B32B 5/08* (2013.01); *B32B 5/266* (2021.05); *B32B 5/271* (2021.05); *B32B 7/02* (2013.01);
(Continued)

(58) Field of Classification Search
None
See application file for complete search history.

(56) References Cited

U.S. PATENT DOCUMENTS 6,967,261 B1 * 11/2005 Soerens ................. A61L 15/46
602/41
10,123,949 B2  11/2018 Mihajlova
(Continued)

FOREIGN PATENT DOCUMENTS

CN  103266421 A  8/2013
CN  107596448 A  1/2018
(Continued)

OTHER PUBLICATIONS

Sugiura T et al., "Novel Bioresorbable Vascular Graft With Sponge Type Scaffold as a Small Diameter Arterial Graft", Ann Thorac Surg. 102,720-727 (2016).
(Continued)

*Primary Examiner* — James C Yager

(57) ABSTRACT

There is provided a porous body which has a first surface and a second surface opposite to each other, and which comprises a first polymer material and a second polymer material, in which a Young's modulus of the first polymer material is lower than a Young's modulus of the second polymer material, an in vivo disappearance rate of the first
(Continued)

polymer material is higher than an in vivo disappearance rate of the second polymer material, and a composition in a first region of the porous body and a composition in a second region of the porous body are different from each other.

16 Claims, 35 Drawing Sheets

(51) Int. Cl.
| | |
|---|---|
| *B32B 7/02* | (2019.01) |
| *A61F 2/82* | (2013.01) |
| *A61L 27/26* | (2006.01) |
| *A61L 27/50* | (2006.01) |
| *A61L 27/56* | (2006.01) |
| *A61L 27/58* | (2006.01) |

(52) U.S. Cl.
CPC ............... *A61F 2/82* (2013.01); *A61L 27/26* (2013.01); *A61L 27/507* (2013.01); *A61L 27/56* (2013.01); *A61L 27/58* (2013.01); *B32B 2250/20* (2013.01); *B32B 2262/0292* (2013.01); *B32B 2262/08* (2013.01); *B32B 2262/124* (2021.05); *B32B 2307/54* (2013.01); *B32B 2307/7163* (2013.01); *B32B 2535/00* (2013.01); *Y10T 428/1352* (2015.01); *Y10T 428/1376* (2015.01)

(56) References Cited

U.S. PATENT DOCUMENTS

| | | | |
|---|---|---|---|
| 10,227,718 B2 | 3/2019 | Cahil | |
| 2002/0173213 A1 | 11/2002 | Chu | |
| 2006/0094320 A1 | 5/2006 | Chen | |
| 2009/0286894 A1* | 11/2009 | Cooper-White | C08J 9/28 521/67 |
| 2009/0311298 A1 | 12/2009 | Nixon | |
| 2010/0254961 A1 | 10/2010 | Nishio | |
| 2012/0029654 A1 | 2/2012 | Xu | |
| 2014/0301971 A1 | 10/2014 | Milbocker | |
| 2018/0221132 A1 | 8/2018 | Nakayama | |
| 2019/0269828 A1 | 9/2019 | Hagihara | |

FOREIGN PATENT DOCUMENTS

| | | |
|---|---|---|
| JP | 2009515569 A | 4/2009 |
| JP | 2012519559 A | 8/2012 |
| JP | 2013534978 A | 9/2013 |
| JP | 2014517070 A | 7/2014 |
| JP | 2017057248 A | 3/2017 |
| JP | 2017080116 A | 5/2017 |
| JP | 6294577 B1 | 3/2018 |
| WO | 2006049663 A1 | 5/2006 |
| WO | 2009031620 A1 | 3/2009 |
| WO | 2016176559 A1 | 11/2016 |
| WO | 2017022750 A1 | 2/2017 |
| WO | 2018021333 A1 | 2/2018 |
| WO | 2018056018 A1 | 3/2018 |

OTHER PUBLICATIONS

Shuhei Tara et al.,"Evaluation of remodeling process in small-diameter cell-free tissue-engineered arterial graft",J. Vasc. Surg. 62,734-743 (2015).

Wang S et.al., "Fabrication of small diametervascular scaffolds by heparin bonded P(LLA CL) composite nanofibers to improve graft patency", International Journal of Nanomedicine, Dove Medical Press, Dove Medical Press, Jun. 7, 2013, vol. 8, 2131-2139.

Young Min Shin et al., "Mussel Inspired Immobilization of Vascular Endothelial Growth Factor (VEGF) for Enhanced Endothelialization of Vascular Grafts", Biomacromolecules. 13, 2020 2028 (201 2).

Tal Dvir et.al., "Prevascularization of cardiac patch on the omentum improves its therapeutic outcome", PNAS. 106, 14990-14995 (2009).

Erik J. Suuronen et al., "An acellular matrix bound ligand enhances t he mobilization, recruitment and therapeutic effects of circulatingprogenitor cells in a hindlimb ischemia model", FASEB J. 23, 1447-1458 (2009).

K.R.Stevens et al., "Physiological function and transplantation of scaffold free and vascularized human cardiac muscle tissue", PNAS. 106, 16568-16573 (2009).

N. Engl. J. Med. 344, 532-533 (2001),Feb. 15, 2001.

M.Kheradmandi et al., "Skeletal muscle regeneration via engineered tissue culture over electrospun nanofibrous chitosan/PVA scaffold", J. Biomed. Mater. Res. Part A J Biomed Mater Res A). 104, 1720-1727 (2016).

B. M.Learoyd et.al, "Alterations with age in theviscoelastic pr operties of human arterial walls", Circ. Res. 18, 278-292 (1966).

Bonani, Walter et al., "Biomolecule Gradient in Micropatterned Nanofibrous Scaffold for Spatiotemporal Release", Langmuir, Sep. 5, 2012, vol. 28, Issue 38, pp. 13675-13687, DOI:10.1021/la302386u.

Elahi Md Fazley et al., "Core-shell Fibers for Biomedical Applications—A Review", Journal of Bioengineering and Biomedical Science, Feb. 4, 2013, vol. 3, Issue 1, article No. 121, DOI:10.4172/2155-9538.1000121.

Narutoshi Hibino et al., "Late-term results of tissue-engineered vascular grafts in humans" 139, 431-436 (2010)(J Thorac Cardiovasc Surg 2010;139:431-6).

Zhang, Y.Z.et al. "Characterization of the Surface Biocompatibility of the Electrospun PCLCollagen Nanofibers Using Fibroblasts", Biomacromolecules, Jul. 27, 2005, vol. 6, Issue 5, pp. 2583-2589, DOI:10.1021/bm050314k.

Kai Wang et al., "Three-Layered PCL Grafts Promoted Vascluar Regeneration in a Rabbit Carotid Artery Model" pp. 608-618.

Gunatillake Pathiraja A et al.,"Biodegradable synthetic polymers for tissue engineering",Cells and Materials,May 20, 2003,vol. 5,pp. 1-16, DOI:10.22203/eCM.v005a01, Table 2.

International Preliminary Report on Patentability for International Application No. PCT/JP2019/022418, drafted by the International Bureau of WIPO on Jun. 26, 2020.

International Search Report and (ISA/237) Written Opinion of the International Search Authority for International Patent Application No. PCT/JP2019/022418, issued/mailed by the Japan Patent Office on Aug. 20, 2019.

Office Action issued for counterpart Japanese Application No. 2020-523156, transmitted from the Japanese Patent Office on Jul. 11, 2023 (drafted on Jun. 30, 2023).

Extended European Search Report for European Patent Application No. 19815108.6, issued by the European Patent Office on Jul. 5, 2021.

* cited by examiner

POROUS BODY AND MATERIAL FOR MEDICAL USE

CROSS-REFERENCE TO RELATED APPLICATIONS

This application is a National Stage Entry of international Application No. PCT/JP2019/022418, filed on Jun. 5, 2019, which claims priority to Japanese Patent application No. 2018-108148, filed on Jun. 5, 2018, the contents of each of which are hereby incorporated by reference in their entirety.

BACKGROUND

1. Technical Field

The present invention relates to a porous body and a material for medical use.

2. Related Art

Expanded polytetrafluoroethylene (ePTFE) is often used as a material for a medical device such as a scaffold. Since ePTFE is flexible and does not show activity on a living body, ePTFE has been applied to many soft tissue materials. On the other hand, ePTFE is difficult to be absorbed by the living body, and has problems such as thrombus formation, calcification, and durability after a long period of time. Therefore, in recent years, application of an absorbable material having high bioabsorbability to a medical device has been studied (refer to, for example, Patent Documents 1 to 6, and Non-Patent Documents 1 to 9).

CITATION LIST

Patent Documents

[Patent Document 1] Japanese Translation of PCT International Publication No. 2012-519559
[Patent Document 2] Japanese Unexamined Patent Application Publication No. 2017-080116
[Patent Document 3] Japanese Patent No. 6294577 Specification [Patent Document 4] Japanese Translation of PCT International Publication No. 2013-534978
[Patent Document 5] Japanese Translation of PCT International Publication No. 2014-517070
[Patent Document 6] Japanese Translation of PCT International Publication No. 2009-515569

Non-Patent Documents

[Non-Patent Document 1] Sugiura T et al., "Novel Bioresorbable Vascular Graft With Sponge-Type Scaffold as a Small-Diameter Arterial Graft", Ann Thorac Surg. 102, 720-727 (2016)
[Non-Patent Document 2] Tara S et al., "Evaluation of remodeling process in small-diameter cell-free tissue-engineered arterial graft", J. Vasc. Surg. 62, 734-743 (2015)
[Non-Patent Document 3] Wang S et. al., "Fabrication of small-diameter vascular scaffolds by heparin-bonded P(LLA-CL) composite nanofibers to improve graft patency", International Journal of Nanomedicine, Dove Medical Press, Dove Medical Press, Jun. 7, 2013, Vol. 8, 2131-2139.
[Non-Patent Document 4] Young Min Shin et.al., "Mussel-Inspired Immobilization of Vascular Endothelial Growth Factor (VEGF) for Enhanced Endothelialization of Vascular Grafts", Biomacromolecules. 13, 2020-2028 (2012)
[Non-Patent Document 5] Tal Dvir et.al., "Prevascularization of cardiac patch on the omentum improves its therapeutic outcome", PNAS. 106, 14990-14995 (2009)
[Non-Patent Document 6] Erik J. Suuronen et.al., "An acellular matrix-bound ligand enhances the mobilization, recruitment and therapeutic effects of circulating progenitor cells in a hindlimb ischemia model", FASEB J. 23, 1447-1458 (2009)
[Non-Patent Document 7] K. R. Stevens et.al., "Physiological function and transplantation of scaffold-free and vascularized human cardiac muscle tissue", PNAS. 106, 16568-16573 (2009)
[Non-Patent Document 8] N. Engl. J. Med. 344, 532-533 (2001), J. Thorac. Cardiovasc. Surg. 139, 431-436 (2010)
[Non-Patent Document 9] M. Kheradmandi et.al., "Skeletal muscle regeneration via engineered tissue culture over electrospun nanofibrous chitosan/PVA scaffold", J. Biomed. Mater. Res. Part A (J Biomed Mater Res A). 104, 1720-1727 (2016)
[Non-Patent Document 10] B. M. Learoyd et.al., "Alterations with age in the viscoelastic properties of human arterial walls", Circ. Res. 18, 278-292 (1966)

Technical Problem

When an absorbable material having high bioabsorbability is applied to a medical device, it is difficult to achieve both an absorption rate of the absorbable material, and strength of the medical device.

GENERAL DISCLOSURE

A first aspect of the present invention provides a porous body. For example, the porous body has a first surface and a second surface opposite to each other. For example, the porous body comprises a second polymer material. In the porous body, for example, a Young's modulus of the porous body determined based on tensile strength in water, in purified water at 37° C., is 0.1 MPa or higher and 10 MPa or lower. In the porous body, for example, (i) a mass loss rate of a first sample, when the first sample that is collected from a first region of the porous body and that has a size of 10 mm×10 mm is immersed in a simulated biological fluid at 35° C. to 39° C. for 30 days, is higher than (ii) a mass loss rate of a second sample, when the second sample that is collected from a second region of the porous body and that has a size of 10 mm×10 mm is immersed in a simulated biological fluid at 35° C. to 39° C. for 30 days. In the porous body, a distance between the first region and the first surface is shorter than a distance between the second region and the first surface.

In the porous body, for example, the second polymer material comprises at least one substance selected from a group consisting of a second biodegradable plastic, a second biopolymer, and a second natural polymer. In the porous body, for example, the second biodegradable plastic is at least one selected from a group consisting of (i) poly (D-lactic acid) (PDLA), poly (L-lactic acid) (PLLA), poly (DL lactic acid) (PDLLA), poly (ε-caprolactone), polyglactin, polyethylene carbonate, and degradable polyurethane, and (ii) at least two copolymers of monomers constituting these, or a copolymer of at least one of the monomers constituting these and another monomer, and (iii) salts and derivatives of these. In the porous body, for example, the second biopolymer is at least one selected from a group consisting of (i) collagen and fibrin, and (ii) at least two copolymers of monomers constituting these, or a copolymer of at least one of the monomers constituting these and another monomer, and (iii) salts and derivatives of these. In the porous body, for example, the second natural polymer is at least one selected from a group consisting of (i) chitin, sericin, fibroin, carboxymethyl cellulose, and chitosan, and (ii) at least two copolymers of monomers constituting these, or a copolymer of at least one of the monomers constituting these and another monomer, and (iii) salts and derivatives of these.

The porous body may comprise a first polymer material having higher biodegradability or bioabsorbability than the second polymer material. In the porous body, an absolute value of a difference between the mass loss rate of the first sample and the mass loss rate of the second sample may be 0.5% or higher. The absolute value of the difference is preferably 0.7% or higher, more preferably 1.0% or higher, further more preferably 1.5% or higher, and further more preferably 2% or higher, further more preferably 2.5% or higher, and further more preferably 3% or higher.

A second aspect of the present invention provides a porous body. For example, the porous body has a first surface and a second surface opposite to each other. For example, the porous body comprises a first polymer material and a second polymer material. In the porous body, for example, a Young's modulus of the first polymer material is lower than a Young's modulus of the second polymer material. In the porous body, for example, an in vivo disappearance rate of the first polymer material is higher than an in vivo disappearance rate of the second polymer material. In the porous body, for example, a composition of the porous body in a first region and a composition of the porous body in a second region are different from each other. In the porous body, for example, a distance between the first region and the first surface is shorter than a distance between the second region and the first surface.

A third aspect of the present invention provides a porous body. For example, the porous body has a first surface and a second surface opposite to each other. For example, the porous body comprises a first polymer material and a second polymer material. In the porous body, for example, a Young's modulus of the first polymer material is lower than a Young's modulus of the second polymer material. In the porous body, for example, absorbability of the first polymer material with respect to phosphate buffered saline is greater, for example, than absorbability of the second polymer material with respect to phosphate buffered saline. In the porous body, for example, a composition of the porous body in a first region and a composition of the porous body in a second region are different from each other. In the porous body, for example, a distance between the first region and the first surface is shorter than a distance between the second region and the first surface.

In the porous body according to the first, the second, and the third aspects, (a) a ratio of a density of the second polymer material to a density of the first polymer material in the first region of the porous body, and (b) a ratio of a density of the second polymer material to a density of the first polymer material in the second region of the porous body may be different from each other. The porous body may include a first surface layer that is porous and is arranged on a surface of the porous body on a first surface side. The porous body may include a support layer that is porous and is arranged on a second surface side of the first surface layer to support the first surface layer. In the porous body, the first region may be arranged on at least a part of the first surface layer. In the porous body, the second region may be arranged on at least a part of the support layer.

In the porous body, each of the first surface layer and the support layer may have a web of a composite fiber that comprises the first polymer material and the second polymer material. In the porous body, (i) a ratio of a mass of the second polymer material to a mass of the first polymer material in the composite fiber of the first region may be smaller than (ii) a ratio of a mass of the second polymer material to a mass of the first polymer material in the composite fiber of the second region.

In the porous body, each of the first surface layer and the support layer may have a web of a composite fiber that comprises the first polymer material and the second polymer material. In the porous body, the composite fiber may have a core-shell structure including a core of the second polymer material and a shell of the first polymer material. In the porous body, (i) a ratio of a diameter or equivalent diameter of the core to a diameter or equivalent diameter of the shell in the composite fiber of the first region may be smaller than (ii) a ratio of a diameter or equivalent diameter of the core to a diameter or equivalent diameter of the shell in the composite fiber of the second region.

In the porous body, (c) a ratio of a density of the second polymer material to a density of the first polymer material in a third region of the porous body, and (b) the ratio of the density of the second polymer material to the density of the first polymer material in the second region of the porous body may be different from each other. In the porous body, a distance between the third region and the first surface may be shorter than the distance between the second region and the first surface. In the porous body, the third region may be arranged on at least a part of the support layer.

The porous body may include a second surface layer that is porous and is arranged on a surface of the porous body on a second surface side. In the porous body, the support layer may be arranged between the first surface layer and the second surface layer. In the porous body, (d) a ratio of a density of the second polymer material to a density of the first polymer material in a fourth region of the porous body, and (b) the ratio of the density of the second polymer material to the density of the first polymer material in the second region of the porous body may be different from each other. In the porous body, a distance between the fourth region and the first surface may be longer than the distance between the second region and the first surface. In the porous body, the fourth region may be arranged on at least a part of the second surface layer. The porous body may have (i) a sheet shape or a film shape, (ii) a tube shape or a roll shape, or (iii) a block shape, a column shape, or a pad shape.

In the porous body, the first polymer material may comprise at least one substance selected from (i) poly(methyl acrylate) (PMA), polymethyl methacrylate (PMMA), polyvinyl alcohol (PVA), hyaluronic acid, alginic acid, poly(glycolic acid)(PGA), polyethylene carbonate (PEC), collagen, fibrin, polyglactin, and chitosan, and (ii) at least two copolymers of monomers constituting these, or a copolymer of at least one of the monomers constituting these and another monomer, and (iii) salts and derivatives of these.

In the porous body, the second polymer material may comprise at least one substance selected from (i) collagen, fibrin, polyglactin, chitosan, chitin, fibroin, sericin, poly (D lactic acid) (PDLA), poly (L lactic acid) (PLLA), poly (DL lactic acid) (PDLLA), poly (ε-caprolactone) (PCL), polyethylene carbonate, polyurethane, and carboxymethyl cellulose, and (ii) at least two copolymers of monomers constituting these, or a copolymer of at least one of the monomers constituting these and another monomer, and (iii) salts and derivatives of these.

In the porous body, the second polymer material may comprise at least one substance selected from (i) carboxymethyl cellulose (CMC), and (ii) at least two copolymers of monomers constituting these, or a copolymer of at least one of the monomers constituting these and another monomer, and (iii) salts and derivatives of these.

In the porous body, the first polymer material may comprise at least one substance selected from a group consisting of a first biodegradable plastic, a first biopolymer, and a first natural polymer. In the porous body, the first biodegradable plastic may be at least one selected from a group consisting of (i) poly(glycolic acid), polyvinyl alcohol, polyglactin, polyethylene carbonate, and degradable polyurethane, and (ii) at least two copolymers of monomers constituting these, or a copolymer of at least one of the monomers constituting these and another monomer, and (iii) salts and derivatives of these. In the porous body, the first biopolymer may be at least one selected from a group consisting of (i) collagen, fibrin, alginic acid, and hyaluronic acid, and (ii) at least two copolymers of monomers constituting these, or a copolymer of at least one of the monomers constituting these and another monomer, and (iii) salts and derivatives of these. In the porous body, the first natural polymer may be at least one selected from a group consisting of (i) chitosan, and (ii) at least two copolymers of monomers constituting these, or a copolymer of at least one of the monomers constituting these and another monomer, and (iii) salts and derivatives of these.

In the porous body, the second polymer material may comprise at least one substance selected from a group consisting of a second biodegradable plastic, a second biopolymer, and a second natural polymer. In the porous body, the second biodegradable plastic may be at least one selected from a group consisting of (i) poly (D-lactic acid) (PDLA), poly (L-lactic acid) (PLLA), poly (DL-lactic acid) (PDLLA), poly (ε-caprolactone), polyglactin, polyethylene carbonate, and degradable polyurethane, and (ii) at least two copolymers of monomers constituting these, or a copolymer of at least one of the monomers constituting these and another monomer, and (iii) salts and derivatives of these. In the porous body, the second biopolymer may be at least one selected from a group consisting of (i) collagen and fibrin, and (ii) at least two copolymers of monomers constituting these, or a copolymer of at least one of the monomers constituting these and another monomer, and (iii) salts and derivatives of these. In the porous body, the second natural polymer may be at least one selected from a group consisting of (i) chitin, sericin, fibroin, carboxymethyl cellulose, and chitosan, and (ii) at least two copolymers of monomers constituting these, or a copolymer of at least one of the monomers constituting these and another monomer, and (iii) salts and derivatives of these.

The porous body comprises a first polymer material and a second polymer material. As the first polymer material, for example, a material which has (i) a Young's modulus lower than that of the second polymer material and which has (ii) an in vivo disappearance rate, or absorbability with respect to the simulated biological fluid higher than that of the second polymer material is selected.

In the porous body, the Young's modulus of the first polymer material is preferably 0.001 MPa or higher and 100 MPa or lower, more preferably 0.01 MPa or higher and 50 MPa or lower, and further more preferably 0.03 MPa or higher and 20 MPa or lower. The Young's modulus of the second polymer material is preferably 0.01 MPa or higher and 2000 MPa or lower, more preferably 0.1 MPa or higher and 1000 MPa or lower, and further more preferably 1 MPa or higher and 500 MPa or lower.

In the porous body, for example, the second polymer material is selected from polymer materials having a Young's modulus of 0.01 MPa or higher and 2000 MPa or lower. On the other hand, the first polymer material is selected from polymer materials having a Young's modulus of 0.001 MPa or higher and 100 MPa or lower, and having a Young's modulus lower than that of the second polymer material.

In the porous body, the in vivo disappearance rate [day/50% mass] of the first polymer material is preferably 1 day or more and 100 days or less, more preferably 1 day or more and 50 days or less, and further more preferably 1 day or more and 30 days or less. The in vivo disappearance rate [day/50% mass] of the second polymer material is preferably 10 days or more and 730 days or less, more preferably 10 days or more and 365 days or less, and further more preferably 20 days or more and 365 days or less.

In the porous body, for example, the second polymer material is selected from polymer materials having an in vivo disappearance rate [day/50% mass] of 10 days or more and 730 days or less. On the other hand, the first polymer material is selected from polymer materials having an in vivo disappearance rate [day/50% mass] of 1 day or more and 100 days or less, and having an in vivo disappearance rate higher than that of the second polymer material.

In the porous body, the absorbability of the first polymer material with respect to phosphate buffered saline is, on the 7th day of immersion, preferably 1% or higher and 90% or lower, more preferably 1% or higher and 70% or lower, and further more preferably 1% or higher and 50% or lower. The absorbability of the second polymer material with respect to phosphate buffered saline may be 0% or higher and 10% or lower on the 7th day of immersion. The absorbability of the second polymer material with respect to phosphate buffered saline is, on the 30th day of immersion, preferably 0% or higher and 60% or lower, more preferably 0% or higher and 50% or lower, and further more preferably 0% or higher and 40% or lower. The absorbability of the second polymer material with respect to phosphate buffered saline is, (i) on the 7th day of immersion, 0% or higher and 10% or lower, and (ii) on the 30th day of immersion, may be 0% or higher and 60% or lower, may be 0% or higher and 50% or lower, and may be 0% or higher and 40% or lower.

In the porous body, for example, the second polymer material is selected from polymer materials having absorbability, with respect to phosphate buffered saline, of 0% or higher and 10% or lower on the 7th day of immersion, and of 0% or higher and 60% or lower on the 30th day of immersion. On the other hand, the first polymer material is selected from polymer materials having absorbability, with respect to phosphate buffered saline, of 1% or higher and 90% or lower on the 7th day of immersion, and having greater absorbability with respect to phosphate buffered saline than that of the second polymer material.

In the porous body, the first polymer material may mainly comprise polyvinyl alcohol, and the second polymer material may mainly comprise fibroin. In the porous body, the first polymer material may mainly comprise polycaprolactone, and the second polymer material may mainly comprise silk fibroin. In the porous body, the first polymer material may mainly comprise polyvinyl alcohol, and the second polymer material may mainly comprise polycaprolactone. In the porous body, examples of a combination of the first polymer material and the second polymer material include (i) polyvinyl alcohol and silk fibroin, (ii) collagen and silk fibroin, (iii) hyaluronic acid and silk fibroin, (iv) alginic acid and silk fibroin, (v) biodegradable polyurethane and silk fibroin, (vi) polyethylene carbonate and silk fibroin, (vii) polyvinyl alcohol and polylactic acid, (viii) collagen and poly (ε-caprolactone), (iX) polyethylene carbonate and polylactic acid, (Xi) polyvinyl alcohol and polylactic acid, (Xii) poly(glycolic acid) and polylactic acid, (Xiii) hyaluronic acid and polylactic acid, and (Xiv) alginic acid and polylactic acid, or the like.

A fourth aspect of the present invention provides a material for medical use. The material for medical use comprises the porous body according to the first, second, or third aspect.

The summary clause does not necessarily describe all necessary features of the embodiments of the present invention. The present invention may also be a sub-combination of the features described above.

DESCRIPTION OF EXEMPLARY EMBODIMENTS

Figure 1:
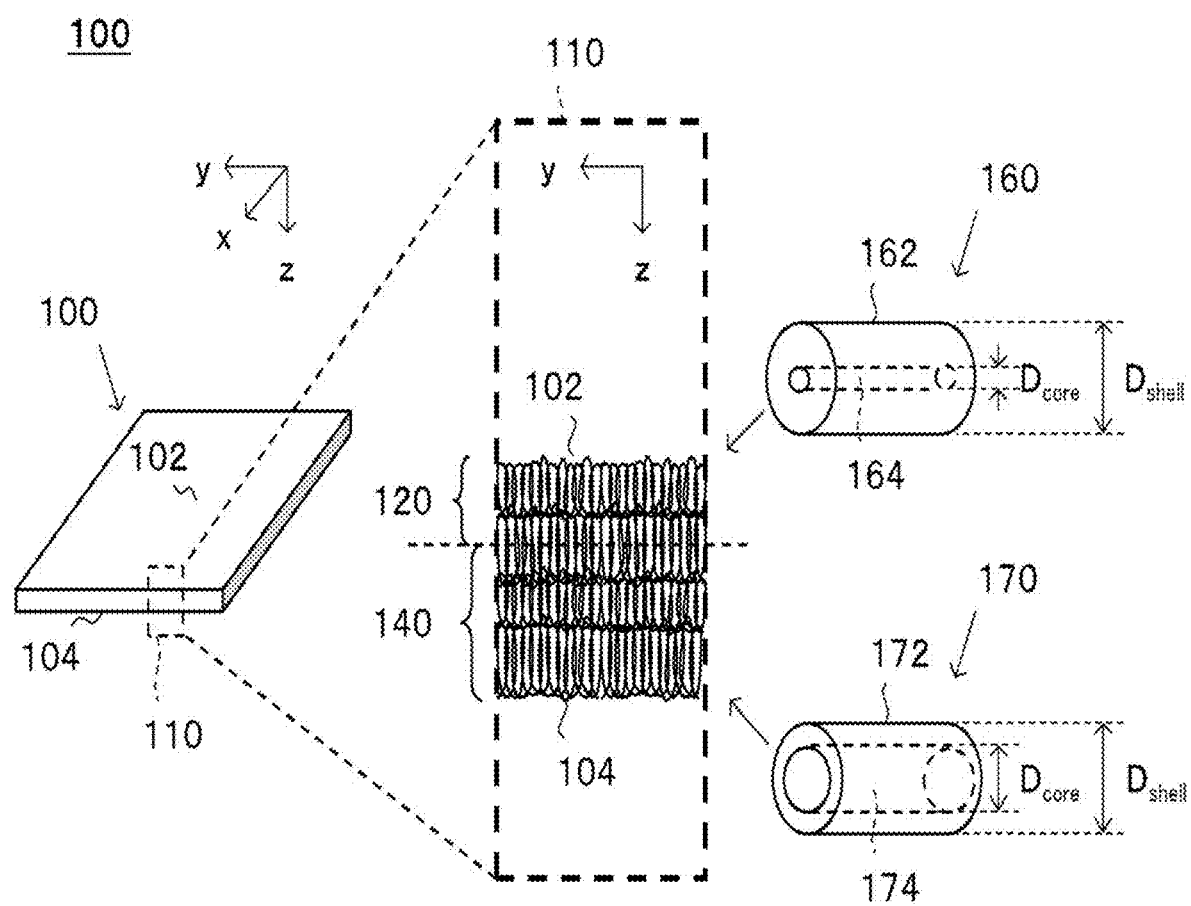
FIG. 1 schematically shows an example of a soft tissue repair material 100.

Hereinafter, the present invention will be described through embodiments of the invention, but the following embodiments do not limit the invention according to the claims. Further, not all the combinations of features described in the embodiments are essential for means to solve the problem in the invention. Note that in the drawings, the same or similar parts may be given the same reference number to omit duplicate description.

[Structure of Soft Tissue Repair Material 100]

FIG. 1 schematically shows an example of a soft tissue repair material 100. FIG. 1 schematically shows an example of an enlarged view of a cross section 110 of the soft tissue repair material 100. FIG. 1 also schematically shows an example of a structure of a fiber 160 arranged in a surface layer region 120, and an example of a structure of a fiber 170 arranged in a support layer region 140.

In the present embodiment as shown in FIG. 1, the soft tissue repair material 100 has a sheet shape. The soft tissue repair material 100 has a surface 102 and a surface 104 opposite to each other. In the present embodiment, the soft tissue repair material 100 may be a nonwoven fabric. The nonwoven fabric is an aggregate of fibers and has a large number of pores.

In the present embodiment, the soft tissue repair material 100 is divided into the surface layer region 120 and the support layer region 140 in the thickness direction (in the figure, the z direction). In the present embodiment, the surface layer region 120 is arranged closer to the surface 102 than the support layer region 140 is. The surface layer region 120 may be a region of the soft tissue repair material 100 on the surface 102 side, and the support layer region 140 may be a region of the soft tissue repair material 100 on a surface 104 side.

A ratio of a thickness of the surface layer region 120 to a thickness of the support layer region 140 is preferably 1:99 to 99:1, and more preferably 20:80 to 80:20. The ratio of the thicknesses of both regions is determined, for example, based on an SEM image of a cross section of the soft tissue repair material 100.

In the present embodiment, the fiber 160 arranged in the surface layer region 120 has a core-shell type of structure. For example, the fiber 160 has a shell portion 162 and a core portion 164. Similarly, the fiber 170 arranged in the support layer region 140 has a core-shell type of structure. For example, the fiber 170 has a shell portion 172 and a core portion 174.

Note that in one embodiment, the fiber 160 and the fiber 170 are respectively parts of long fibers or filaments different from each other. In another embodiment, the fiber 160 and the fiber 170 may be different parts of the same long fiber or filament.

The soft tissue repair material 100 may be an example of a porous body and a material for medical use. The surface 102 may be an example of a first surface. The surface 104 may be an example of a second surface. The surface layer region 120 may be an example of a surface layer. The support layer region 140 may be an example of a support layer. The fiber 160 may be an example of a composite fiber. The fiber 170 may be an example of a composite fiber.

In the present embodiment, the soft tissue repair material 100 will be described in detail by using, as an example, a case where each of the surface layer region 120 and the support layer region 140 is a region obtained by virtually dividing one nonwoven fabric at any position of the nonwoven fabric in the thickness direction. In this case, a porous layered object is arranged in each of the surface layer region 120 and the support layer region 140. Further, one fiber may constitute a part of the surface layer region 120, and a part of the support layer region 140. However, the structure of the soft tissue repair material 100 is not limited to the present embodiment.

In another embodiment, the surface layer region 120 and the support layer region 140 may be respectively porous layers which are different from each other in at least one of a composition and a structure. Further, the porous layer constituting the surface layer region 120, and the porous layer constituting the support layer region 140 may be integrated by any method. For example, when the surface layer region 120 and the support layer region 140 are respectively nonwoven fabrics, both are integrated by a known method such as a thermal bonding method, a chemical bonding method, a needle punching method, and a water flow entanglement method. The shape of the porous layer may be (i) a nonwoven fabric shape, and may be (ii) a foam shape, a sponge shape, or a monolith shape.

Further, in the present embodiment, the soft tissue repair material 100 will be described in detail by using, as an example, a case where the surface layer region 120 and the support layer region 140 are in contact with each other. However, the structure of the soft tissue repair material 100 is not limited to the present embodiment. In another embodiment, between the surface layer region 120 and the support layer region 140, another type of region may be arranged. Further, another type of region may be arranged between the surface 102 and the surface layer region 120, and another type of region may be arranged between the surface 104 and the support layer region 140.

[Composition of Soft Tissue Repair Material 100]

In the present embodiment, the soft tissue repair material 100 comprises two or more types of polymer materials. For example, the soft tissue repair material 100 comprises a first polymer material and a second polymer material. Each of the surface layer region 120 and the support layer region 140 may respectively comprises the first polymer material and the second polymer material. In the present embodiment, a composition of the soft tissue repair material 100 in the surface layer region 120, and a composition of the soft tissue repair material 100 in the support layer region 140 are different from each other. For example, a ratio of the first polymer material and the second polymer material in the surface layer region 120, and a ratio of the first polymer material and the second polymer material in the support layer region 140 are different from each other. The above described ratio may be a ratio of a mass or a density in each material.

[Physical Properties of First Polymer Material and Second Polymer Material]

The first polymer material and the second polymer material are preferably materials having high biocompatibility, low toxicity, and high safety. The first polymer material and the second polymer material are preferably materials having relatively high bioabsorbability. The first polymer material and the second polymer material may comprise at least one selected from a bioabsorbable polymer, a bioabsorbable copolymer, and salts and derivatives of these. The bioabsorbable polymer and the bioabsorbable copolymer may be polymer compounds that are degraded by a degrading enzyme or a metabolic system in vivo, or polymer compounds that are hydrolyzed non-specifically in vivo.

For example, the first polymer material and the second polymer material independently comprises at least one selected from (i) polysaccharides such as cellulose, hyaluronic acid, alginic acid, chitin, chitosan, glycosaminoglycans, chondroitin sulfate, and heparin, (ii) peptides or proteins such as collagen, gelatin, sericin, casein, fibrin, keratin, and fibroin, (iii) polymers or copolymers such as acrylic resin, polycarbonate, polyvinyl alcohol (PVA), polyester, and polyurethane, and (iv) salts and derivatives of these. Fibroin may be silk fibroin. Sericin may be silk sericin. Each of the first polymer material and the second polymer material may be a composite material comprising the above described substances. Each of the first polymer material and the second polymer material may be a composite material comprising the above described substances as raw materials.

Examples of a derivative of cellulose include carboxymethyl cellulose. Examples of acrylic resin include poly(methyl acrylate) (PMA), polymethyl methacrylate (PMMA), or the like. Examples of polycarbonate include polyethylene carbonate. Polyester may be aliphatic polyester, may be aromatic polyester, and may be copolymerized polyester.

Examples of polyester include (i) polylactic acid (D, L or DL form) (PLA), poly(glycolic acid) (PGA), poly (ε-caprolactone)(PCL), polydioxanone (PDX, PDS or PDO), polyhydroxyalkanoate (PHA), polyhydroxybutyrate (PHB), polybutylene succinate (PBS), and poly(butyl acrylate) (PBA), poly(ethyl acrylate)(PEA), and (ii) at least two copolymers of monomers constituting these, or a copolymer of at least one of the monomers constituting these and another monomer, and (iii) salts and derivatives of these. Examples of the above described copolymer include (i) PBST, PBAT, or PEAT obtained by introducing a terephthalate unit to PBS, PBA or PEA, (ii) glycolide-lactide copolymer (polyglactin, PLGA), (iii) glycolide-ε-caprolactone copolymer (polyglycapron), (iv) lactide (D, L, DL form)-ε-caprolactone copolymer, (v) glycolide-lactide (D, L, DL form)-ε-caprolactone copolymer, or the like.

The first polymer material and the second polymer material are preferably materials having Young's moduli (sometimes referred to as a tensile elastic modulus) different from each other. For example, the Young's modulus of the first polymer material is lower than the Young's modulus of the second polymer material. The Young's modulus of the polymer material can be adjusted by a molecular weight of the polymer material, a mixing ratio of the monomers constituting the polymer material, or the like.

The Young's modulus of the polymer material is calculated, for example, according to ISO 527-1 and JIS K 7161. Specifically, first, a 40 mm×5 mm test piece of a polymer material to be measured is prepared. In addition, a thickness of the test piece in a dry state is measured. The thickness of the test piece may be a thickness of one spot of the test piece, and may be an average value of thicknesses of a plurality of spots. Then, in an atmosphere of 20° C., a tensile load of 10 mm/min is applied to the test piece, and while the test piece is pulled in the long side direction thereof, tensile stress (sometimes referred to as normal stress) and strain (sometimes referred to as elongation) are measured.

The tensile stress [MPa] is calculated by dividing the tensile load [N] by a cross-sectional area [mm$^2$] of the test piece before the test starts. The above described cross-sectional area is an area of a surface obtained by cutting the test piece in a plane substantially perpendicular to the tensile direction. In addition, the strain [%] is calculated by the following Mathematical Expression 1.

$$\text{Strain [\%]}=100\times(L-Lo)/Lo \qquad \text{[Math 1]}$$

In Math. 1, Lo is a length of the sample before the test starts, and L is a length of the sample at the time of the test.

The Young's modulus is calculated as a ratio of the tensile stress to the strain within a tensile proportional limit (sometimes referred to as an elastic range). In the present embodiment, the Young's modulus is calculated from a slope of a tangent of an SS curve (sometimes referred to as a stress-strain diagram). The slope of the tangent is calculated from, for example, stress data for a strain of 1% to 4%. Note that when it is difficult to calculate the Young's modulus based on the above described procedure due to circumstances of the sample, or the like, the Young's modulus may be calculated based on a procedure described in relation to Example described below.

For example, in JIS K 7161, a state of the test piece (sometimes referred to as the sample) is adjusted according to specifications of a material to be tested. Unless otherwise specified regarding the adjustment of the state of the test piece, the state is recommended to be adjusted for 16 hours or more under conditions of a temperature of 21° C. to 25° C. and a humidity of 40% to 60%. However, depending on the material, physical properties may vary greatly between a wet state and a dry state. Examples of the above described materials include (i) biopolymers such as collagen, fibrin, alginic acid, hyaluronic acid, fibroin (for example, silk fibroin), and sericin (for example, silk sericin), (ii) polyvinyl alcohol, poly(glycolic acid), polyglactin, or the like. Therefore, in such a case for example, the Young's modulus is calculated based on tensile testing in water described below.

The Young's modulus of the first polymer material is preferably 0.001 MPa or higher and 100 MPa or lower, more preferably 0.01 MPa or higher and 50 MPa or lower, and further more preferably 0.03 MPa or higher and 20 MPa or lower. The Young's modulus of the second polymer material is preferably 0.01 MPa or higher and 2000 MPa or lower, more preferably 0.1 MPa or higher and 1000 MPa or lower, and further more preferably 1 MPa or higher and 500 MPa or lower.

For example, the second polymer material is selected from polymer materials having a Young's modulus of 0.01 MPa or higher and 2000 MPa or lower. On the other hand, the first polymer material is selected from polymer materials having a Young's modulus of 0.001 MPa or higher and 100 MPa or lower, and having a Young's modulus lower than that of the second polymer material.

The first polymer material and the second polymer material are preferably materials having in vivo disappearance rates different from each other. For example, the in vivo disappearance rate of the first polymer material is higher than the in vivo disappearance rate of the second polymer material. The in vivo disappearance rate of the polymer material can be adjusted by a molecular weight of the polymer material, a mixing ratio of the monomers constituting the polymer material, or the like. The in vivo disappearance rate is expressed, for example, as a period [days/50% mass] until 50% of a mass disappears in vivo. In this case, the smaller the above described period, the higher the in vivo disappearance rate.

The in vivo disappearance rate [day/50% mass] of the polymer material is calculated, for example, based on the following procedure. First, a test piece of a polymer material to be measured is prepared. A shape of the test piece is set to be a pellet shape with a diameter of 20 mm and a thickness of 0.6 mm. Then, dorsal skin of an anesthetized mouse is incised and the test piece is embedded. After a certain period of time has passed, the test piece is taken out from an embedding site, and the test piece is cleaned with purified water. The cleaned test piece is sufficiently dried, and then a mass of the test piece is measured. Then, the above described operation is repeated until a mass loss rate calculated by the following Mathematical Expression 2 becomes lower than 50%.

$$\text{Mass loss rate [\%]}=100\times(Wo-W)/Wo \qquad \text{[Math. 2]}$$

In Mathematical Expression 2, Wo is a mass of the test piece before the test starts, and W is a mass of the test piece after embedding for a certain period of time. A period until the mass loss rate reaches 50% is estimated by data fitting, and the estimated value is calculated as the disappearance rate.

The in vivo disappearance rate [day/50% mass] of the first polymer material is preferably 1 day or more and 100 days or less, more preferably 1 day or more and 50 days or less, and further more preferably 1 day or more and 30 days or less. The in vivo disappearance rate [day/50% mass] of the second polymer material is preferably 10 days or more and 730 days or less, more preferably 10 days or more and 365 days or less, and further more preferably 20 days or more and 365 days or less.

For example, the second polymer material is selected from polymer materials having an in vivo disappearance rate [day/50% mass] of 10 days or more and 730 days or less. On the other hand, the first polymer material is selected from polymer materials having an in vivo disappearance rate [day/50% mass] of 1 day or more and 100 days or less, and having an in vivo disappearance rate higher than that of the second polymer material.

The first polymer material and the second polymer material are preferably materials having each different absorbability with respect to a simulated biological fluid. For example, the absorbability of the first polymer material with respect to the simulated biological fluid is greater than the absorbability of the second polymer material with respect to the simulated biological fluid. The absorbability with respect to the simulated biological fluid is an index that correlates with the in vivo disappearance rate of the polymer material. The absorbability with respect to the simulated biological fluid can be adjusted by a molecular weight of the polymer material, a mixing ratio of the monomers constituting the polymer material, or the like.

For example, as the absorbability of the polymer material with respect to the simulated biological fluid, absorbability with respect to phosphate buffered saline (sometimes referred to as PBS) is used. The absorbability with respect to phosphate buffered saline is calculated, for example, based on the procedure described in relation to Example described below.

The absorbability of the first polymer material with respect to phosphate buffered saline is, on the 7th day of immersion, preferably 1% or higher and 90% or lower, more preferably 1% or higher and 70% or lower, and further more preferably 1% or higher and 50% or lower. The absorbability of the second polymer material with respect to phosphate buffered saline may be 0% or higher and 10% or lower on the 7th day of immersion. The absorbability of the second polymer material with respect to phosphate buffered saline is, on the 30th day of immersion, preferably 0% or higher and 60% or lower, more preferably 0% or higher and 50% or lower, and further more preferably 0% or higher and 40% or lower. The absorbability of the second polymer material with respect to phosphate buffered saline is, (i) on the 7th day of immersion, 0% or higher and 10% or lower, and (ii) on the 30th day of immersion, may be 0% or higher and 60% or lower, may be 0% or higher and 50% or lower, and may be 0% or higher and 40% or lower.

For example, the second polymer material is selected from polymer materials having absorbability, with respect to phosphate buffered saline, of 0% or higher and 10% or lower on the 7th day of immersion, and of 0% or higher and 60% or lower on the 30th day of immersion. On the other hand, the first polymer material is selected from polymer materials having absorbability, with respect to phosphate buffered saline, of 1% or higher and 90% or lower on the 7th day of immersion, and having greater absorbability with respect to phosphate buffered saline than that of the second polymer material.

[Combination of First Polymer Material and Second Polymer Material]

As described above, the soft tissue repair material 100 comprises the first polymer material and the second polymer material. As the first polymer material, for example, a material which has (i) a Young's modulus lower than that of the second polymer material and which has (ii) an in vivo disappearance rate, or absorbability with respect to the simulated biological fluid higher than that of the second polymer material is selected.

Examples of a material which has an in vivo disappearance rate or absorbability with respect to the simulated biological fluid that is very high include poly(methyl acrylate)(PMA), polyvinyl alcohol (PVA), hyaluronic acid, alginic acid, poly(glycolic acid) (PGA), or the like. These materials have in vivo disappearance rates [days/50% mass] of approximately less than 30 days.

Examples of a material which has an in vivo disappearance rate or absorbability with respect to the simulated biological fluid that is relatively high include polyethylene carbonate, collagen, fibrin, polyglactin, chitosan, or the like. These materials have in vivo disappearance rates [days/50% mass] of approximately 30 days or more and less than 90 days.

Examples of a material which has an in vivo disappearance rate or absorbability with respect to the simulated biological fluid that is relatively low include poly (D-lactic acid) (PDLA), poly (L-lactic acid) (PLLA), poly (ε-caprolactone) (PCL), poly (DL-lactic acid) (PDLLA), chitin, fibroin, sericin, or the like. These materials have in vivo disappearance rates [days/50% mass] of approximately 90 days or more. Fibroin may be silk fibroin. Sericin may be silk sericin.

In consideration of the in vivo disappearance rate or the absorbability with respect to the simulated biological fluid, and the Young's modulus, the first polymer material comprises, for example, at least one substance selected from (i) poly(methyl acrylate) (PMA), polymethyl methacrylate (PMMA), polyvinyl alcohol (PVA), hyaluronic acid, alginic acid, poly(glycolic acid)(PGA), polyethylene carbonate, collagen, fibrin, polyglactin, and chitosan, and (ii) at least two copolymers of monomers constituting these, or a copolymer of at least one of the monomers constituting these and another monomer, and (iii) salts and derivatives of these. The first polymer material may be a composite material comprising at least one of the above described substances, and may be a composite material comprising at least one of the above substances as a raw material.

In consideration of the in vivo disappearance rate or the absorbability with respect to the simulated biological fluid, and the Young's modulus, the second polymer material comprises, for example, at least one substance selected from (i) collagen, fibrin, polyglactin, chitosan, chitin, fibroin, sericin, poly (D-lactic acid) (PDLA), poly (L-lactic acid) (PLLA), poly (DL-lactic acid) (PDLLA), poly (ε-caprolactone) (PCL), polyethylene carbonate, and polyurethane, and (ii) at least two copolymers of monomers constituting these, or a copolymer of at least one of the monomers constituting these and another monomer, and (iii) salts and derivatives of these. Fibroin may be silk fibroin. Sericin may be silk sericin. The second polymer material may comprise bioabsorbable polyester other than the above. The second polymer material may be a composite material comprising at least one of the above described substances, and may be a composite material comprising at least one of the above substances as a raw material.

Note that carboxymethyl cellulose is degraded relatively quickly in the environment, but on the other hand, is degraded relatively gently in the living body. Further, strength of carboxymethyl cellulose varies greatly between a dry state and a water containing state. For example, the glass transition temperature of carboxymethyl cellulose is about 135° C. in a dry state, but decreases down to approximately −60° C. as the water content increases. Considering the above, carboxymethyl cellulose can be used as a raw material for the second polymer material.

In one embodiment, the first polymer material mainly comprises polyvinyl alcohol, and the second polymer material mainly comprises fibroin. In another embodiment, the first polymer material mainly comprises polycaprolactone, and the second polymer material mainly comprises silk fibroin. In still another embodiment, the first polymer material mainly comprises polyvinyl alcohol, and the second polymer material mainly comprises polycaprolactone.

Fibroin imparts high tensile strength to a material comprising fibroin. Therefore, the second polymer material preferably comprises fibroin. In one embodiment, fibroin may be silk fibroin derived from natural silk produced by a silkworm or a spider. Fibroin is preferably silk fibroin derived from silk (sometimes referred to as silkworm silk) produced by a silkworm. In another embodiment, fibroin may be derived from silk protein produced by genetic engineering. Examples of silk proteins produced by genetic engineering can include silk proteins produced by bacteria, yeasts, animal and plant cells, transgenic plants, transgenic animals, or the like, which are genetically modified to produce silk proteins.

In silkworm silk, fibroin is coated with sericin. Fibroin, which is derived from natural silkworm silk, is obtained by removing sericin from silkworm silk. In one embodiment, the composition may comprise, as an impurity, 10% to 35% by mass of sericin with respect to a mass of fibroin. In another embodiment, a content of sericin in the composition is, with respect to the mass of fibroin, preferably lower than 20% (mass ratio), more preferably lower than 10% (mass ratio), and further more preferably lower than 5% (mass ratio).

In another embodiment, the first polymer material comprises, for example, at least one substance selected from a group consisting of a first biodegradable plastic, a first biopolymer, and a first natural polymer. Further, the second polymer material comprises, for example, at least one substance selected from a group consisting of a second biodegradable plastic, a second biopolymer, and a second natural polymer. In a specific combination of the first polymer material and the second polymer material, for example, the first polymer material and the second polymer material are selected such that a Young's modulus of the first polymer material as a simple substance is lower than a Young's modulus of the second polymer material as a simple substance, and biodegradability or bioabsorbability of the first polymer material as a simple substance is better than biodegradability or bioabsorbability of the second polymer material as a simple substance.

The first biodegradable plastic is, for example, at least one selected from a group consisting of (i) poly(glycolic acid), polyvinyl alcohol, polyglactin, polyethylene carbonate, and degradable polyurethane, and (ii) at least two copolymers of monomers constituting these, or a copolymer of at least one of the monomers constituting these and another monomer, and (iii) salts and derivatives of these. The first biodegradable plastic may be, for example, at least one selected from a group consisting of poly(glycolic acid), polyvinyl alcohol, polyglactin, polyethylene carbonate, and degradable polyurethane, and salts and derivatives of these.

The first biopolymer is, for example, at least one selected from a group consisting of (i) collagen, fibrin, alginic acid, and hyaluronic acid, and (ii) at least two copolymers of monomers constituting these, or a copolymer of at least one of the monomers constituting these and another monomer, and (iii) salts and derivatives of these. The first biopolymer may be at least one selected from a group consisting of collagen, fibrin, alginic acid, and hyaluronic acid, and salts and derivatives of these.

The first natural polymer is, for example, at least one selected from a group consisting of (i) chitosan, and (ii) at least two copolymers of monomers constituting these, or a copolymer of at least one of the monomers constituting these and another monomer, and (iii) salts and derivatives of these. The first natural polymer may be at least one selected from a group consisting of chitosan, and salts and derivatives of these.

The second biodegradable plastic is, for example, at least one selected from a group consisting of (i) poly (D-lactic acid) (PDLA), poly (L-lactic acid) (PLLA), poly (DL-lactic acid) (PDLLA), poly (ε-caprolactone)(sometimes referred to as PCL), polyglactin, polyethylene carbonate, and degradable polyurethane, and (ii) at least two copolymers of monomers constituting these, or a copolymer of at least one of the monomers constituting these and another monomer, and (iii) salts and derivatives of these. The second biodegradable plastic may be at least one selected from a group consisting of poly (D-lactic acid) (PDLA), poly (L-lactic acid) (PLLA), poly (DL-lactic acid) (PDLLA), poly (ε-caprolactone)(PCL), polyglactin, polyethylene carbonate, and degradable polyurethane, and salts and derivatives of these.

The second biopolymer is, for example, at least one selected from a group consisting of (i) collagen and fibrin, and (ii) at least two copolymers of monomers constituting these, or a copolymer of at least one of the monomers constituting these and another monomer, and (iii) salts and derivatives of these. The second biopolymer may be at least one selected from a group consisting of collagen and fibrin, and salts and derivatives of these.

The second natural polymer is, for example, at least one selected from a group consisting of (i) chitin, sericin (for example, silk sericin), fibroin (for example, silk fibroin), carboxymethyl cellulose, and chitosan, and (ii) at least two copolymers of monomers constituting these, or a copolymer of at least one of the monomers constituting these and another monomer, and (iii) salts and derivatives of these. The second natural polymer may be at least one selected from a group consisting of chitin, sericin, fibroin, carboxymethyl cellulose, and chitosan, and salts and derivatives of these.

Note that when the substances, which are listed as specific examples of the first biodegradable plastic, the first biopolymer, the first natural polymer, the second biodegradable plastic, the second biopolymer, or the second natural polymer, are classified into a hard material and a soft material, for example, based on the glass transition temperature of each substance, classification into three categories is possible, the categories being (i) a hard material of which the glass transition temperature is sufficiently higher than room temperature, (ii) a soft material of which the glass transition temperature is approximately the same as room temperature or lower than room temperature, and (iii) an amphoteric material that can be a hard material or a soft material depending on a molding method, water content, or the like. Then, in the hard material and the amphoteric material, a substance having relatively high biodegradability or bioabsorbability can be used as a raw material for the first polymer material or the second polymer material. In the hard material and the amphoteric material, a substance having relatively poor biodegradability or bioabsorbability can be used as a raw material for the second polymer material. In the soft material, a substance having relatively high biodegradability or bioabsorbability can be used as a raw material for the first polymer material. In the soft material, a substance having relatively poor biodegradability or bioabsorbability can be used as a raw material for the first polymer material or the second polymer material.

Examples of the above described hard material include polylactic acid, chitin and chitosan, and salts and derivatives of these, or the like. The glass transition temperatures of polylactic acid, chitin and chitosan are, for example, 60° C., higher than 240° C., and 140° C. to 203° C., respectively. Comparing the biodegradability or the bioabsorbability among these substances, chitosan is excellent in biodegradability or bioabsorbability in comparison with polylactic acid and chitin. For example, for chitosan, the above described in vivo disappearance rate [day/50% mass] is 9 weeks to 52 weeks (57 days or more and 364 days or less), and the above described absorbability with respect to phosphate buffered saline is higher than 5% on the 7th day of immersion (that is, in an immersion period of 168 hours or more and less than 192 hours). On the other hand, for each of polylactic acid and chitin, the above described in vivo disappearance rate [day/50% mass] is 53 weeks or more (365 days or more), and the above described absorbability with respect to phosphate buffered saline is higher than 0% and 5% or lower on the 7th day of immersion.

Examples of the soft material include poly(glycolic acid), polyvinyl alcohol, polyethylene carbonate, degradable polyurethane, collagen, fibrin, and alginic acid, hyaluronic acid, and salts and derivatives of these, or the like. The glass transition temperatures of poly(glycolic acid), polyvinyl alcohol, polyethylene carbonate, and degradable polyurethane are, for example, 37° C., lower than 5° C., 27° C., and −20° C., respectively. Comparing the biodegradability or the bioabsorbability among these substances, poly(glycolic acid), polyvinyl alcohol, alginic acid and hyaluronic acid are excellent in biodegradability or bioabsorbability in comparison with other substances. For example, for each of poly (glycolic acid), polyvinyl alcohol, alginic acid and hyaluronic acid, the above described in vivo disappearance rate [day/50% mass] is 1 week to 8 weeks (1 day or more and 56 days or less), and the above described absorbability with respect to phosphate buffered saline is higher than 10% on the 7th day of immersion. On the other hand, for each of polyethylene carbonate, degradable polyurethane, collagen, and fibrin, the above described in vivo disappearance rate [day/50% mass] is 9 weeks to 52 weeks (57 days or more and 364 days or less), and the above described absorbability with respect to phosphate buffered saline is higher than 5% and 10% or lower on the 7th day of immersion.

Examples of the above described amphoteric material include polyglactin, poly(ε-caprolactone), sericin, fibroin, and carboxymethyl cellulose, and salts and derivatives of these, or the like. The glass transition temperatures of polyglactin, poly (ε-caprolactone), sericin, fibroin, and carboxymethyl cellulose are, for example, approximately 40° C., approximately −60° C. (different depending on the water content), approximately 170° C. (different depending on the water content), approximately 178° C. (different depending on the water content), and −60° C. to 135° C. (different depending on the water content), respectively. Comparing the biodegradability or the bioabsorbability among these substances, polyglactin is excellent in biodegradability or bioabsorbability in comparison with other substances. For example, for polyglactin, the above described in vivo disappearance rate [day/50% mass] is 1 week to 8 weeks (1 day or more and 56 days or less), and the above described absorbability with respect to phosphate buffered saline is higher than 5% on the 7th day of immersion. On the other hand, for each of poly(ε-caprolactone), sericin, fibroin, and carboxymethyl cellulose, the above described in vivo disappearance rate [day/50% mass] is 9 weeks to 52 weeks (57 days or more and 364 days or less), and the above described absorbability with respect to phosphate buffered saline is 5% or lower on the 7th day of immersion.

Specific examples of the combination of the first polymer material and the second polymer material satisfying the above described condition include (i) polyvinyl alcohol and silk fibroin, (ii) collagen and silk fibroin, (iii) hyaluronic acid and silk fibroin, (iv) alginic acid and silk fibroin, (v) biodegradable polyurethane and silk fibroin, (vi) polyethylene carbonate and silk fibroin, (vii) polyvinyl alcohol and polylactic acid, (viii) collagen and poly (ε-caprolactone), (iX) polyethylene carbonate and polylactic acid, (Xi) polyvinyl alcohol and polylactic acid, (Xii) poly(glycolic acid) and polylactic acid, (Xiii) hyaluronic acid and polylactic acid, and (Xiv) alginic acid and polylactic acid, or the like. Note that the above described polylactic acid may be poly (D-lactic acid), may be poly (L-lactic acid), may be poly (DL-lactic acid), and may be a mixture of these.

When the Young's modulus, a degree of hardness or softness, or the biodegradability or the bioabsorbability, or the like of the first polymer material greatly varies due to a variation in a parameter such as the molecular weight of the material contained in the first polymer material and a functional group introduced into the material, the above described parameter relating to the first polymer material may be determined such that the Young's modulus, the degree of hardness or softness, or the biodegradability or the bioabsorbability of the first polymer material satisfies the above described condition. Similarly, when the Young's modulus, a degree of hardness or softness, or the biodegradability or the bioabsorbability of the second polymer material greatly varies due to a variation in a parameter such as the molecular weight of the material contained in the second polymer material and a functional group introduced into the material, the above described parameter relating to the second polymer material may be determined such that the Young's modulus, the degree of hardness or softness, or the biodegradability or the bioabsorbability of the second polymer material satisfies the above described condition.

By using, as raw materials, (i) the second polymer material that has a relatively high Young's modulus as a simple substance, and has relatively good biodegradability or bioabsorbability as a simple substance, and (ii) the first polymer material that has a lower Young's modulus than the second polymer material as a simple substance, but has better biodegradability or bioabsorbability than the second polymer material as a simple substance, as described above, and producing a porous body, a material having high biocompatibility and strength can be obtained. The above described material has properties particularly suitable for a material for medical use.

When the soft tissue repair material 100 is embedded in the living body, the soft tissue repair material 100 functions as a scaffold for a biological tissue to regenerate. With the present embodiment, the second polymer material is absorbed into the living body at a relatively early stage. Therefore, proliferation of a cell that proliferates in the early stage of the regeneration of the biological tissue is not inhibited, and the regeneration of the biological tissue is promoted. Further, thrombus formation, calcification, or the like after a long period of time is suppressed. On the other hand, the first polymer material remains in the living body for a longer period of time than the second polymer material. Further, since the first polymer material has a relatively high Young's modulus, strength of the soft tissue repair material 100 (for example, at least one of breaking strength and breaking elongation) is maintained until the biological tissue sufficiently regenerates. Further, when the soft tissue repair material 100 and a blood vessel, an organ, or the like are sutured, a suture retention ability, a suturing property, or the like improves.

For example, in regeneration of a blood vessel tissue by using a scaffold, it is conceivable that (i) blood vessel remodeling progresses centering on a scaffold surface, and (ii) collagen deposition progresses due to cell infiltration from the outside of the scaffold. Then, a step of blood vessel remodeling is roughly divided into two phases: (i) acute phase, and (ii) subacute phase/chronic phase.

The acute phase is a period of up to approximately 8 weeks after embedding. In the acute phase, infiltration of inflammatory cells into the scaffold occurs and endothelialization occurs on a luminal surface of the scaffold. Further, vascular smooth muscle cells are generated following the endothelialization, and the vascular smooth muscle cells surround the endothelium. The subacute phase/chronic phase is a period after approximately 8 weeks have passed after embedding. In the subacute phase/chronic phase, as the scaffold is degraded and absorbed, the vascular smooth muscle cells gradually proliferate from a lumen side and a smooth muscle layer thickens.

In a case where the soft tissue repair material 100 according to the present embodiment is used as a blood vessel remodeling material, when the soft tissue repair material 100 is initially embedded in the living body, the inflammatory cells or the like infiltrates into pores surrounded by the second polymer material, and endothelialization is promoted. Further, in a stage where the vascular smooth muscle cells proliferate, the degradation/absorption of the second polymer material also progresses to a considerable degree. Therefore, inhibition of the proliferation of vascular smooth muscle cells by the second polymer material is suppressed. When the blood vessel remodeling is in the subacute phase/chronic phase, the degradation/absorption of the first polymer material also progresses, and the inhibition of the proliferation of vascular smooth muscle cells by the first polymer material is suppressed.

[Composition Distribution in Thickness Direction]

In the present embodiment, the composition of the soft tissue repair material 100 varies depending on a position in the thickness direction of the soft tissue repair material 100. For example, a composition of the soft tissue repair material 100 in at least a part of the surface layer region 120, and a composition of the soft tissue repair material 100 in at least a part of the support layer region 140 are different from each other. That is, (a) a ratio of a density of the second polymer material to a density of the first polymer material in at least a part of the surface layer region 120, and (b) a ratio of a density of the second polymer material to a density of the first polymer material in at least a part of the support layer region 140 are different from each other.

Note that the density of the second polymer material in at least a part of the surface layer region 120 may be smaller than the density of the second polymer material in at least a part of the support layer region 140. Further, the density of the second polymer material in at least a part of the surface layer region 120 may be higher than 0. The density of the second polymer material in at least a part of the surface layer region 120 may be 0.

The above described density may be an apparent density, and may be a bulk density. An apparent density of each polymer material in each region of the soft tissue repair material 100 is calculated, for example, by multiplying an apparent density of a sample collected from each region of the soft tissue repair material 100 by a component ratio of each polymer material in the region. A bulk density of each polymer material in each region of the soft tissue repair material 100 is calculated, for example, by multiplying a bulk density of a sample collected from each region of the soft tissue repair material 100 by a component ratio of each polymer material in the region. By setting the conditions to be constant, the conditions being for measuring the density and the component ratio of the sample collected from each region, it is possible to determine a magnitude relationship between density ratios of the first polymer material and the second polymer material in each region.

The apparent density of the sample is determined, for example, by an immersion method. The immersion method may be a water immersion method. The bulk density of the sample is determined, for example, by a dimensional method. The apparent density or the bulk density of the sample may be determined by using a value of a true density. The apparent density or the bulk density of the sample may be determined based on porosity (sometimes referred to as porosity) and the true density of the sample. The porosity of the sample is determined, for example, by image analysis of the surface or the cross section of the sample. The above described image may be an SEM image, and may be a µCT image. The true density of the sample is determined, for example, by a pycnometer method (sometimes referred to as a specific gravity bottle method).

The component ratio of each polymer material in the sample is determined, for example, by the $^1$H-NMR spectrum of the sample surface. The component ratio of each polymer material may be a mass ratio based on a mass of the entire sample, or may be a mass ratio based on a mass of a specific component.

At least a part of the surface layer region 120 may be a region having a predetermined area and a predetermined thickness from the surface 102. At least a part of the support layer region 140 may be a region having a predetermined area and a predetermined thickness from the surface 104. The above described area may be an area on the xy plane in FIG. 1. At least a part of the surface layer region 120 may be an example of a first region. At least a part of the support layer region 140 may be an example of a second region.

The composition of the soft tissue repair material 100 in at least a part of the surface layer region 120 is determined, for example, by an FT-IR measurement of the surface 102 of the soft tissue repair material 100 by a total reflection method. The composition of the soft tissue repair material 100 in at least a part of the support layer region 140 is determined, for example, by an FT-IR measurement of the surface 104 of the soft tissue repair material 100 by a total reflection method. Details of the ATR-FTIR measurement will be described in relation to Example described below.

The soft tissue repair material 100 may have two or more compositions, or may have three or more compositions in the thickness direction thereof. According to one embodiment, a content ratio of a specific component increases continuously or stepwise in the thickness direction of the soft tissue repair material 100. According to another embodiment, a content ratio of a specific component decreases continuously or stepwise in the thickness direction of the soft tissue repair material 100.

[Physical Properties of Soft Tissue Repair Material 100]

The Young's modulus of the soft tissue repair material 100 is, for example when the Young's modulus is determined based on a result of tensile testing in water described in relation to the physical property evaluation of Example described below, preferably 0.1 MPa or higher and 10 MPa or lower, preferably 0.1 MPa or higher and 5 MPa or lower, preferably 0.2 MPa or higher and 5 MPa or lower, preferably 0.3 MPa or higher and 3 MPa or lower, preferably 0.3 MPa or higher and 2.5 MPa or lower, and preferably 0.35 MPa or higher and 2 MPa or lower. This makes it possible to obtain, for example, the soft tissue repair material 100 showing a Young's modulus lower than that of an artificial blood vessel made of expanded polytetrafluoroethylene (ePTFE), and having physical properties closer to those of a human artery in Young's modulus.

The Young's modulus of the soft tissue repair material 100 is specifically determined based on tensile strength in water in purified water at 37° C. For example, when the soft tissue repair material 100 is a sheet shaped material, a test piece used for tensile testing in water is collected such that a profile of the test piece (sometimes referred to as a sample) in the thickness direction reflects a profile of the sheet shaped soft tissue repair material 100 in the thickness direction. More specifically, from the vicinity of the center of the soft tissue repair material 100, a test piece that has a size of 15 mm×3 mm and that has a thickness equivalent to the thickness of the soft tissue repair material 100 at a collected portion of the test piece is collected.

When the soft tissue repair material 100 is a tube shaped material, for example, first, a part of the soft tissue repair material 100 is cut along the extension direction of the tube shaped soft tissue repair material 100. Then, by deploying the tube shaped soft tissue repair material 100 by using a notch, the sheet shaped soft tissue repair material 100 can be obtained. Subsequently, by using the sheet shaped soft tissue repair material 100, the test piece is collected according to the procedure described above. Details of the tensile testing in water and the procedure for calculating the Young's modulus will be described below in relation to the physical property evaluation of Example.

As described above, in the soft tissue repair material 100 in the thickness direction, composition ratios of the first polymer material and the second polymer material are different from each other. Then, as a raw material of the first polymer material, a substance having higher biodegradability or bioabsorbability than a raw material of the second polymer material is used. Therefore, for example, (i) a mass loss rate of a first sample, when the first sample that is collected from the first region of the soft tissue repair material 100 and that has a size of 10 mm×10 mm is immersed in a simulated biological fluid at 35° C. to 39° C. for 30 days, is higher than (ii) a mass loss rate of a second sample, when the second sample that is collected from the second region of the soft tissue repair material 100 and that has a size of 10 mm×10 mm is immersed in a simulated biological fluid at 35° C. to 39° C. for 30 days.

An absolute value of a difference between the mass loss rate of the first sample and the mass loss rate of the second sample may be 0.5% or higher. In this case, for example, a content or a density of the first polymer material on one surface side of the soft tissue repair material 100 is higher than a content or a density of the first polymer material on the other surface side. As a result, for example, it is possible to produce a sheet in which the degradation or the absorption progresses from one side of the sheet into the living body.

The absolute value of the difference described above is preferably 0.7% or higher, more preferably 1.0% or higher, further more preferably 1.5% or higher, further more preferably 2% or higher, further more preferably 2.5% or higher, and further more preferably 3% or higher. The difference of the absolute values described above can be appropriately set according to use of the soft tissue repair material 100. When the absolute value of the difference described above is 0.5% or higher, for example, a porous body particularly suitable for a material for medical use to prevent adhesion is produced. When the absolute value of the difference described above is 1% or higher, for example, a porous body particularly suitable for a material for medical use for an artificial blood vessel can be produced. Further, when the absolute value of the difference described above is 1.5% or higher, for example, a porous body particularly suitable for a material for medical use for a wound covering material can be produced. Note that the use of the soft tissue repair material 100 is not limited to these.

Note that during the immersion period of the test piece for the mass loss rate, a temperature of the simulated biological fluid is controlled to be around 37° C. This makes it possible for the temperature of the simulated biological fluid to be controlled within a range of 35° C. to 39° C. Details of the method for calculating the mass loss rate, and the simulated biological fluid will be described in relation to the degradability evaluation of Example described below.

Further, a shortest distance between the first region and the first surface of the soft tissue repair material 100 is shorter than a distance between the second region and the first surface. Thereby, in the profile of the soft tissue repair material 100 in the thickness direction, two samples corresponding to two different ranges are prepared. For example, the first sample is collected from a first surface side of the soft tissue repair material 100, and the second sample is collected from a second surface side which is opposite to the first surface. Note that the expression that the first surface and the second surface are opposite to each other is not limited to a case where the first surface and the second surface are substantially parallel.

According to one embodiment, first, the soft tissue repair material 100 is cut to be substantially parallel to the first surface, and the soft tissue repair material 100 is divided into a slice on the first surface side and a slice on the second surface side. The slice on the first surface side and the slice on the second surface side preferably have the thickness of the same degree. Then, a test piece having a size of 10 mm×10 mm is cut out from the slice on the first surface side, and a first sample is prepared. Similarly, a test piece having a size of 10 mm×10 mm is cut out from the slice on the second surface side, and a second sample is prepared.

Note that the soft tissue repair material 100 may be divided into three or more slices. Further, the first sample and the second sample may be prepared by using two slices of the three or more slices. In this case, the slice from which the first sample is collected and the slice from which the second sample is collected preferably have the thickness of the same degree.

According to another embodiment, a test piece having a size of 10 mm×10 mm is cut out from one part of the soft tissue repair material 100. By a method such as polishing or cutting, a part of the cut out test piece on the second surface side is removed such that a thickness of the test piece is reduced. Thereby, the first sample is prepared. Similarly, a test piece having a size of 10 mm×10 mm is cut out from another part of the soft tissue repair material 100. By a method such as polishing or cutting, a part of the cut out test piece on the first surface side is removed such that a thickness of the test piece is reduced.

Note that when the first sample is prepared, a part of the cut out test piece on the first surface side and a part of the test piece on the second surface side may be removed such that the thickness of the test piece is reduced. Similarly, when the second sample is prepared, a part of the cut out test piece on the first surface side and a part of the test piece on the second surface side may be removed such that the thickness of the test piece is reduced.

In these embodiments, the first sample and the second sample are prepared, for example, to have masses of about 15 mg in a dry state. The masses of the first sample and the second sample in a dry state may be 10 mg or more and 20 mg or less. Within the numerical range described above, an influence on the measurement of the mass loss rate can be suppressed. Note that the first sample and the second sample are preferably collected from a region where the thickness of the soft tissue repair material 100 is substantially uniform in a dry state.

When the thickness of the soft tissue repair material 100 is not sufficient, and a mass of a single first sample in a dry state is less than 15 mg, the first sample may be prepared by collecting, from the soft tissue repair material 100, a plurality of first samples having substantially the same position in the thickness direction of the soft tissue repair material 100 such that a total mass of the plurality of first samples in the dry state is about 15 mg. Similarly, when the thickness of the soft tissue repair material 100 is not sufficient, and a mass of a single second sample in a dry state is less than 15 mg, the second sample may be prepared by collecting, from the soft tissue repair material 100, a plurality of second samples having substantially the same position in the thickness direction of the soft tissue repair material 100 such that a total mass of the plurality of second samples in the dry state is about 15 mg.

Further, the thicknesses of the first sample and the second sample are not particularly limited; however, the thicknesses of the first sample and the second sample are, in dry states, preferably approximately 20 μm to 200 μm, more preferably approximately 40 μm to 180 μm, further more preferably approximately 40 μm to 120 μm, and further more preferably approximately 50 μm to 100 μm. Within the numerical range described above, an influence on the measurement of the mass loss rate can be suppressed. The thickness of each sample may be an average value of thicknesses at three points substantially arranged on a diagonal line on the sample. Examples of the above described three points include a substantially center portion of the sample, and two points spaced from each side of the sample by about 2.5 mm.

[Use of Soft Tissue Repair Material 100]

The soft tissue repair material 100 can be used in a variety of medical devices. Examples of the use of the soft tissue repair material 100 include an artificial blood vessel, an aortic repair sheet, an inferior vena cava repair sheet, an artificial pericardium, a heart defect patching material, a bile duct patching material, a stent graft outer fabric, a stent graft of a transcatheter aortic valve implantation (TAVI), an artificial dura mater, an artificial peritoneum, an artificial pleura, or the like. Examples of the artificial blood vessel include a small-diameter artery graft, a medium-diameter artery graft, a vein graft, or the like. The soft tissue repair material 100 may be used as a material for a medical device to repair a tissue of a circulatory system. For example, when the soft tissue repair material 100 is used as a material for an artificial blood vessel, a medical device that can reproduce a regeneration model of the blood vessel tissue obtained by using the described above scaffold can be provided.

Note that in the present embodiment, an example of the porous body has been described by using the sheet shaped soft tissue repair material 100 as an example. However, the porous body is not limited to the soft tissue repair material 100 according to the present embodiment. In another embodiment, the porous body may have (i) a sheet shape or a film shape, (ii) a tube shape or a roll shape, or (iii) a block shape, a column shape, or a pad shape. The tube shaped porous body may be a hollow rolled body, and the column shaped porous body may be a solid rolled body. Cross-sectional shapes of the tube shaped porous body and the column shaped porous body are not particularly limited. Examples of the above described cross-sectional shape include a circle, an ellipse, a polygon, a free curve, a combination of these, and the like.

[Structure of Fiber Constituting Soft Tissue Repair Material 100]

Figure 2:
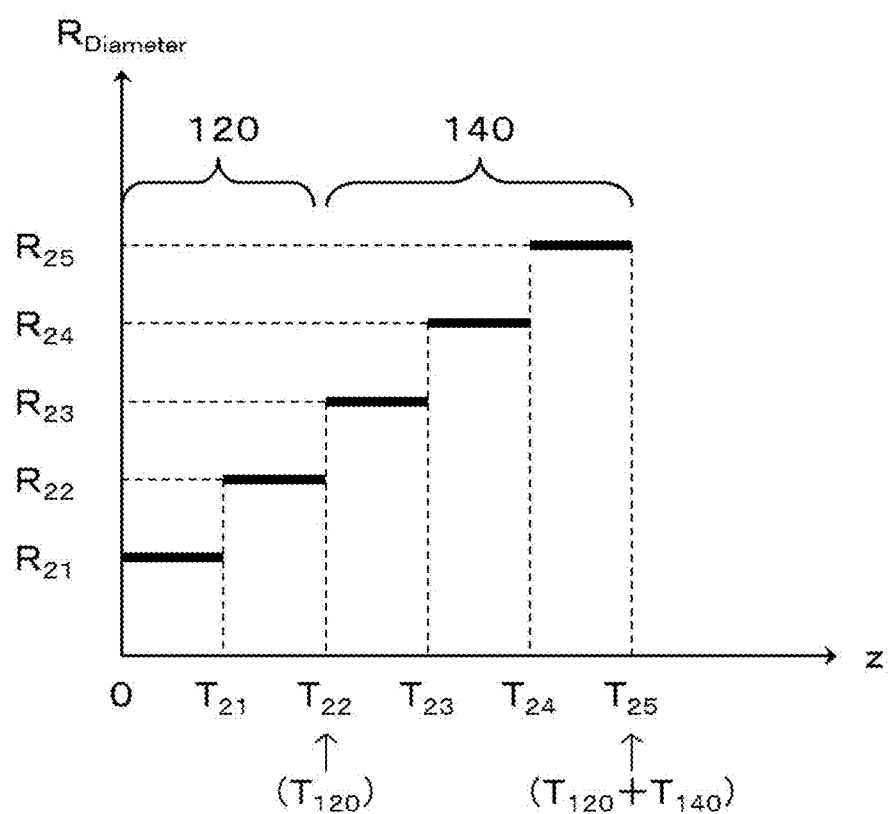
FIG. 2 schematically shows an example of a composition profile of the soft tissue repair material 100.
Figure 3:
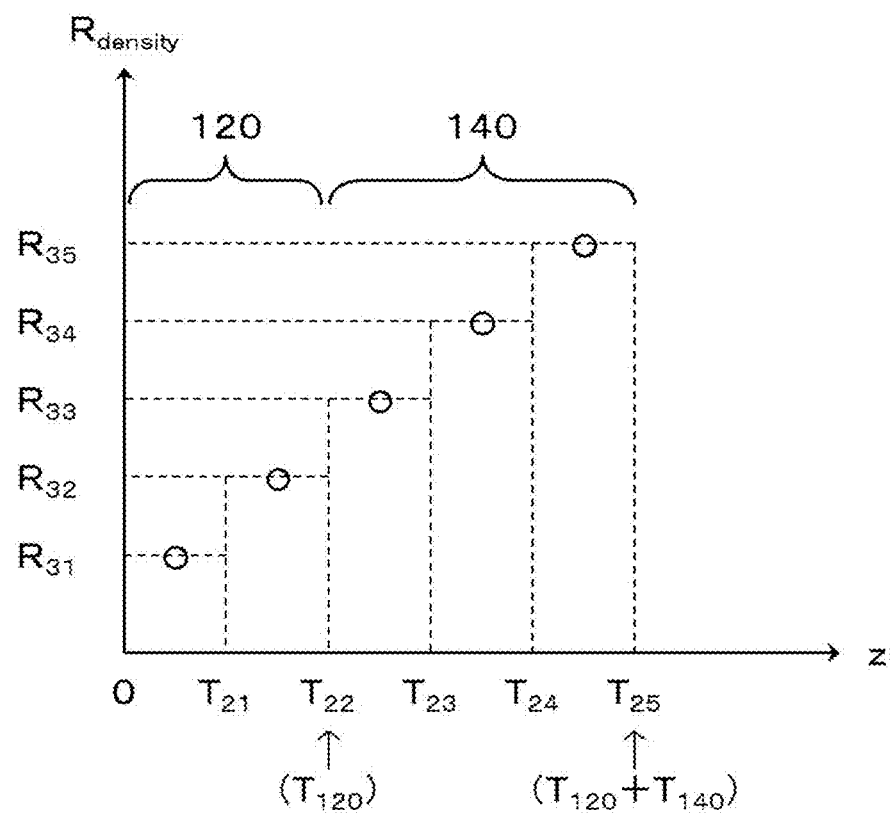
FIG. 3 schematically shows an example of a physical property profile of the soft tissue repair material 100.

Structural details of the fiber 160 and fiber 170 will be described by using FIG. 2 and FIG. 3. FIG. 2 schematically shows an example of a composition profile of the soft tissue repair material 100. FIG. 3 schematically shows an example of a physical property profile of the soft tissue repair material 100.

According to the present embodiment, the compositions of the fiber 160 and the fiber 170 are different from each other. As a result, the composition of the soft tissue repair material 100 varies depending on a position in the thickness direction of the soft tissue repair material 100. At least one of the fiber 160 and the fiber 170 may comprise two or more polymer materials. For example, a composition of a material constituting the shell portion 162 and a composition of a material constituting the core portion 164 are different from each other. A composition of a material constituting the shell portion 172 and a composition of a material constituting the core portion 174 may be different from each other.

In the present embodiment, the core portion 164 and the core portion 174 are constituted, for example, by the second polymer material. Further, the shell portion 162 and the shell portion 172 are constituted, for example, by the first polymer material. The composition of the material constituting the shell portion 162 and the composition of the material constituting the shell portion 172 may be the same, and may be different from each other. The composition of the material constituting the core portion 164 and the composition of the material constituting the core portion 174 may be the same, and may be different from each other.

As shown in FIG. 2, according to the present embodiment, (i) a ratio ($R_{Diameter}$) of the diameter or equivalent diameter $D_{core}$ of the core portion 164 to the diameter or equivalent diameter D of the shell portion 162, and (ii) a ratio ($R_{Diameter}$) of the diameter or equivalent diameter $D_{core}$ of the core portion 174 to the diameter or equivalent diameter D of the shell portion 172 are different from each other. Thereby, as shown in FIG. 3, (a) a ratio ($R_{density}$) of a density of the second polymer material to a density of the first polymer material in at least a part of the surface layer region 120, and (b) a ratio ($R_{density}$) of a density of the second polymer material to a density of the first polymer material in at least a part of the support layer region 140 are different from each other.

In FIG. 2, the horizontal axis represents a position from the surface 102 in the thickness direction, and the vertical axis represents the $R_{Diameter}$ at each position. Further, in FIG. 2, $T_{120}$ indicates a thickness of the surface layer region 120, and $T_{140}$ indicates a thickness of the support layer region 140.

As shown in FIG. 2, in the present embodiment, a value of $R_{Diameter}$ increases stepwise from the surface 102 toward the surface 104. According to the present embodiment, the value of $R_{Diameter}$ increases stepwise from the surface 102 toward the surface 104 inside the surface layer region 120 as well. Further, the value of $R_{Diameter}$ increases stepwise from the surface 102 toward the surface 104 inside the support layer region 140 as well.

As shown in FIG. 2, (i) the ratio ($R_{Diameter}$) of the diameter or equivalent diameter of the core to the diameter or equivalent diameter of the shell in the fiber 160 is smaller than (ii) a ratio ($R_{Diameter}$) of the diameter or equivalent diameter of the core to the diameter or equivalent diameter of the shell in the fiber 170. Accordingly, (i) a ratio of a mass of the second polymer material to a mass of the first polymer material in the fiber 160 is smaller than (ii) a ratio of a mass of the second polymer material to a mass of the first polymer material in the fiber 170.

Further, for example, (c) a ratio of a density of the second polymer material to a density of the first polymer material in a region inside the support layer region 140, and (b) a ratio of a density of the second polymer material to a density of the first polymer material in a region of the support layer region 140 in the vicinity of the surface 104 are different from each other. The region inside the support layer region 140 may be an example of a third region.

In FIG. 3, the horizontal axis represents a position from the surface 102 in the thickness direction, and the vertical axis represents the $R_{density}$ at each position. For example, from FIG. 3, it can be seen that at the position of z=0 to $T_{21}$, the ratio $R_{density}$ of the density [g/cm$^3$] of the second polymer to the density [g/cm$^3$] of the first polymer is $R_{31}$. As shown in FIG. 2 and FIG. 3, as $R_{Diameter}$ in FIG. 2 increases, the value of $R_{density}$ in FIG. 3 also increases.

According to the present embodiment, an aggregate of fibers having a large content of the first polymer (sometimes referred to as a web, a fleece, or the like) is arranged on the surface 102 side. Further, on the surface 104 side, an aggregate of fibers having a large content of the second polymer is arranged. This makes it possible to obtain a tissue repair material that can induce a tissue regeneration. In particular, a graft material that can reproduce the above described blood vessel remodeling hypothesis can be obtained. With the above described graft material, blood vessel regeneration can be appropriately induced.

Figure 4:
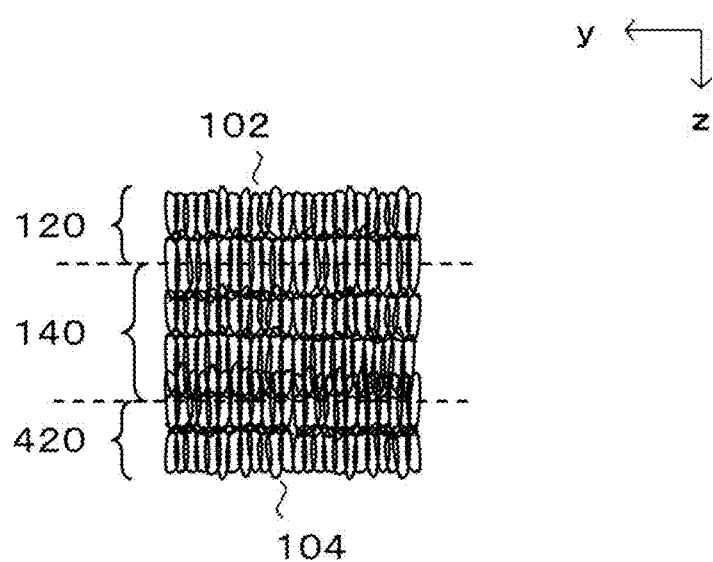
FIG. 4 schematically shows an example of a soft tissue repair material 400.
Figure 5:
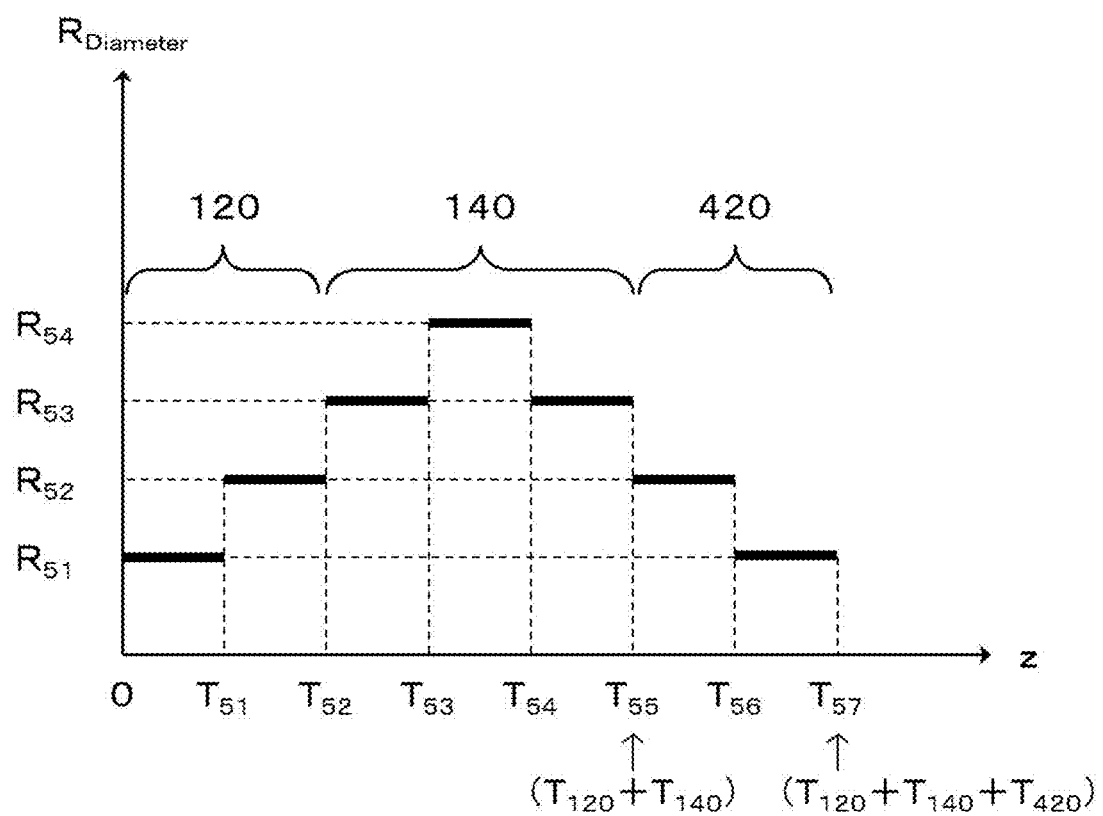
FIG. 5 schematically shows an example of a composition profile of the soft tissue repair material 400.

Another example of the soft tissue repair material will be described by using FIG. 4 and FIG. 5. FIG. 4 schematically shows an example of a soft tissue repair material 400. FIG. 5 schematically shows an example of a composition profile of the soft tissue repair material 400.

As shown in FIG. 4, in the present embodiment, the soft tissue repair material 400 includes the surface layer region 120, the support layer region 140, and a surface layer region 420. The surface layer region 420 may have a configuration similar to that of the surface layer region 120. The surface layer region 420 may be an example of a second surface layer.

The soft tissue repair material 400 is different from the soft tissue repair material 100 in that the support layer region 140 is arranged between the surface layer region 120 and the surface layer region 420 so as to support the surface layer region 120 and the surface layer region 420. The soft tissue repair material 400 may have a configuration similar to that of the soft tissue repair material 100 except for the above described difference.

In the present embodiment, each of the surface layer region 120, the support layer region 140, and the surface layer region 420 has a nonwoven fabric having a web of a composite fiber that comprises the first polymer material and the second polymer material. The composite fiber may have a core-shell structure including the core of the second polymer material and the shell of the first polymer material. The surface layer region 120 is arranged on the surface 102 side of the support layer region 140, and the surface layer region 420 is arranged on the surface 104 side of the support layer region 140.

As shown in FIG. 5, in the present embodiment, (d) a ratio of a density of the second polymer material to a density of the first polymer material in at least a part of the surface layer region 420, and (b) a ratio of a density of the second polymer material to a density of the first polymer material in at least a part of the support layer region 140 are different from each other. For example, (d) a ratio of a density of the second polymer material to a density of the first polymer material in at least a part of the surface layer region 420 is smaller than (b) a ratio of a density of the second polymer material to a density of the first polymer material in at least a part of the support layer region 140. At least a part of the surface layer region 420 may be an example of a fourth region.

Figure 6:
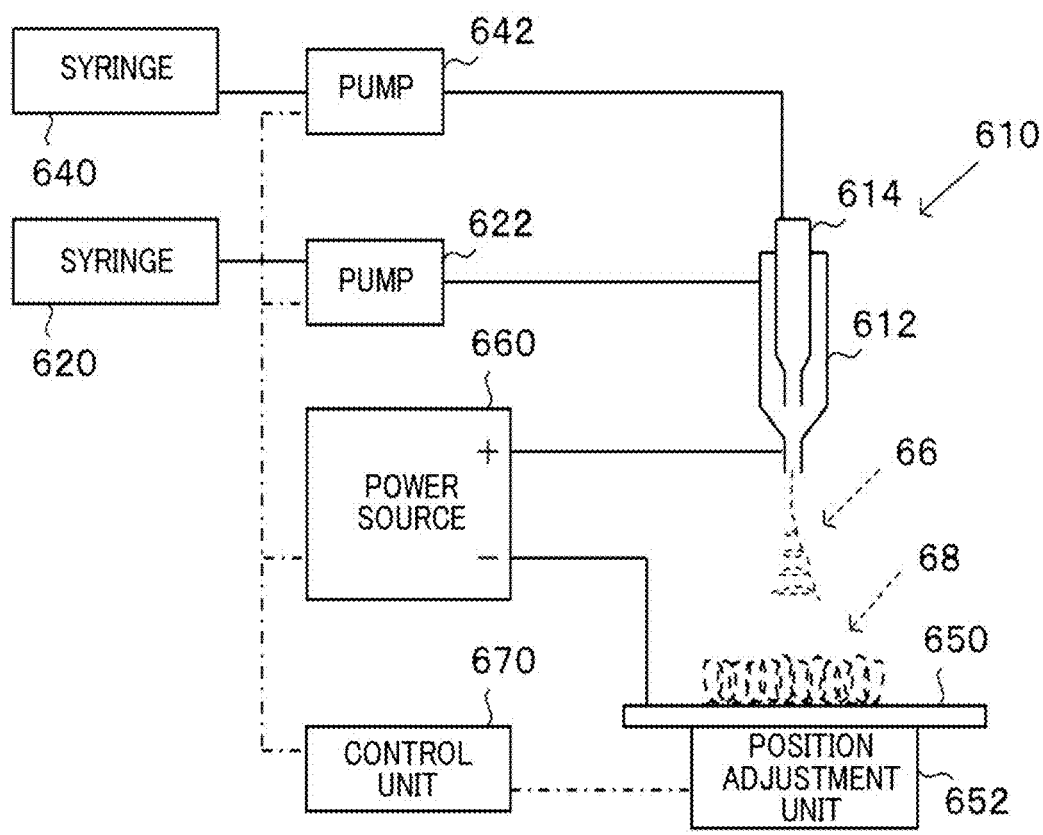
FIG. 6 schematically shows an example of a system configuration of an electrospinning system 600.

FIG. 6 schematically shows an example of a system configuration of an electrospinning system 600. In the present embodiment, the electrospinning system 600 includes a core shell nozzle 610, a syringe 620, a pump 622, a syringe 640, a pump 642, a collector plate 650, a position adjustment unit 652, a power source 660, and a control unit 670. In the present embodiment, the core shell nozzle 610 has an outer cylinder 612 and an inner cylinder 614.

In the present embodiment, the core shell nozzle 610 ejects a spinning jet 66 of a fiber having a core-shell structure. In the present embodiment, the outer cylinder 612 and the inner cylinder 614 are coaxially arranged. A discharge outlet of the inner cylinder 614 is arranged inside the outer cylinder 612. The discharge outlet of the inner cylinder 614 is arranged, for example, in the vicinity of the discharge outlet of the outer cylinder 612.

A first solution stored in the syringe 620 is supplied to the outer cylinder 612 via the pump 622. A second solution stored in the syringe 640 is supplied to the inner cylinder 614 via the pump 642. The second solution supplied to the inner cylinder 614 is discharged from the discharge outlet of the inner cylinder 614, and then mixed with the first solution supplied to the outer cylinder 612. Note that the structure of the core shell nozzle 610 is not limited to the present embodiment. The core shell nozzle 610 may be a nozzle of a double cylinder type, and may be a nozzle of a side by side type.

A positive voltage is applied, by the power source 660, to the vicinity of the discharge outlet of the outer cylinder 612. Thereby, liquid droplets containing the first solution and the second solution are discharged from the discharge outlet of the outer cylinder 612, and then ejected toward the collector plate 650 as the spinning jet 66. As a result, a web 68 is formed on the collector plate 650.

In the present embodiment, the syringe 620 stores a solution of the first polymer (sometimes referred to as the first solution). A solvent may be water, may be an organic solvent, and may be various types of mixed solvents. The pump 622 transfers the first solution stored in the syringe 620 to the outer cylinder 612.

In the present embodiment, the syringe 640 stores a solution of the second polymer (sometimes referred to as the second solution). A solvent may be water, may be an organic solvent, and may be various types of mixed solvents. The pump 642 transfers the second solution stored in the syringe 640 to the inner cylinder 614.

In the present embodiment, the collector plate 650 aggregates the spinning jet 66 discharged from the core shell nozzle 610. The collector plate 650 is electrically connected, for example, to a ground terminal of the power source 660. In the present embodiment, the position adjustment unit 652 adjusts a relative position between the core shell nozzle 610 and the collector plate 650. In the present embodiment, the power source 660 applies the positive voltage to the core shell nozzle 610.

In the present embodiment, the control unit 670 controls an operation of the electrospinning system 600. For example, the control unit 670 controls a discharge amount of at least one of the pump 622 and the pump 642. The control unit 670 controls the position adjustment unit 652 to adjust the relative position between the core shell nozzle 610 and the collector plate 650. The control unit 670 controls the power source 660 to adjust a potential difference between the core shell nozzle 610 and the collector plate 650.

Figure 7:
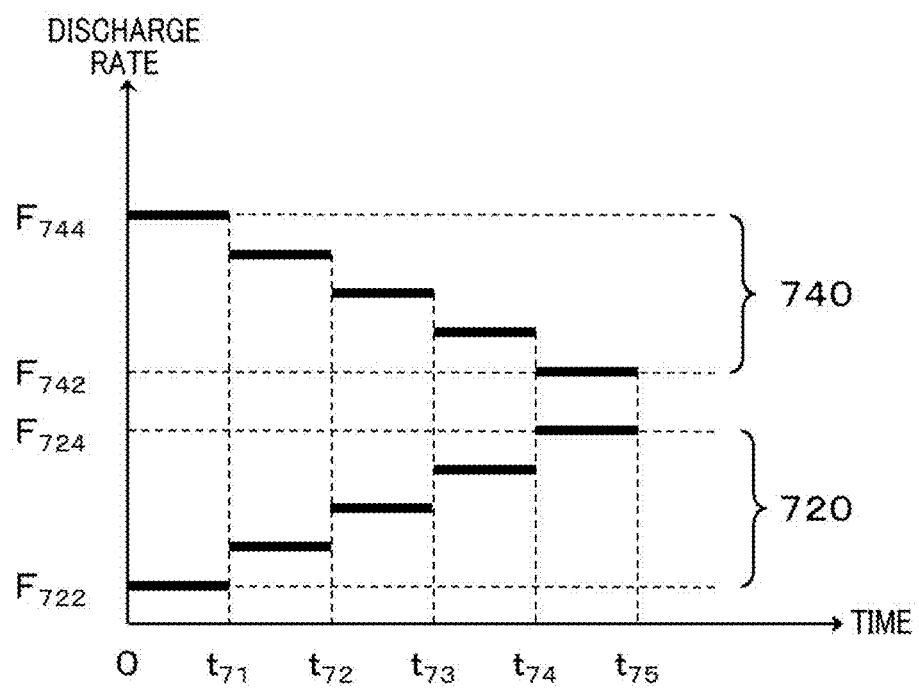
FIG. 7 schematically shows an example of a control pattern 700.
Figure 8:
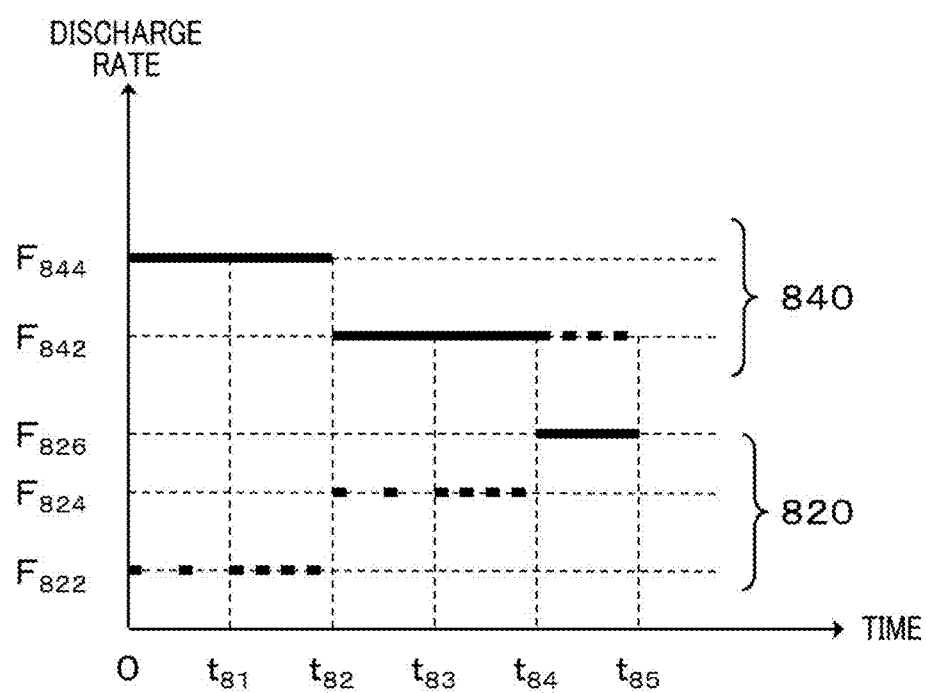
FIG. 8 schematically shows an example of a control pattern 800.

An example of the control by the control unit 670 will be described by using FIG. 7 and FIG. 8. FIG. 7 schematically shows an example of a control pattern 700 relating to the pump 622 and the pump 642. FIG. 8 schematically shows an example of a control pattern 800 relating to the pump 622 and the pump 642.

As shown in FIG. 7, a control pattern 720 may be information in which a timing at which the pump 622 operates (for example, $t_{71}$ to $t_{75}$), and a target value of a discharge rate (sometimes referred to as the discharge amount) of the pump 622 at that timing are associated with each other. Similarly, a control pattern 740 may be information in which a timing at which the pump 642 operates, and a target value of a discharge rate of the pump 642 at that timing are associated with each other.

In the present embodiment, with the passage of time, the discharge rate of the pump 622 increases stepwise, and the discharge rate of the pump 642 decreases stepwise. Thereby, for example, when the electrospinning system 600 initially starts the operation, the web 68 of fibers having a relatively large diameter of the core portion in comparison with the diameter of the shell portion is deposited. Subsequently, in the fibers constituting the web 68, the ratio of the diameter of the core portion to the diameter of the shell portion gradually decreases. As a result, the soft tissue repair material 100 is produced. By changing the control pattern, the electrospinning system 600 can also produce the soft tissue repair material 400.

As shown in FIG. 8, a control pattern 820 may be information in which a timing at which the pump 622 operates (for example, $t_{81}$ to $t_{85}$), and a target value of a discharge rate (sometimes referred to as the discharge amount) of the pump 622 at that timing are associated with each other. Similarly, a control pattern 840 may be information in which a timing at which the pump 642 operates, and a target value of a discharge rate of the pump 642 at that timing are associated with each other.

The control pattern 800 is different from the control pattern 700 in that the control unit 670 controls a ratio of on/off of the pump in a unit period so as to adjust the ratio of the diameter of the core portion to the diameter of the shell portion in the fibers which constitutes the web 68. This makes it possible for the electrospinning system 600 to produce a nonwoven fabric such as the soft tissue repair material 100 and the soft tissue repair material 400.

Figure 9:
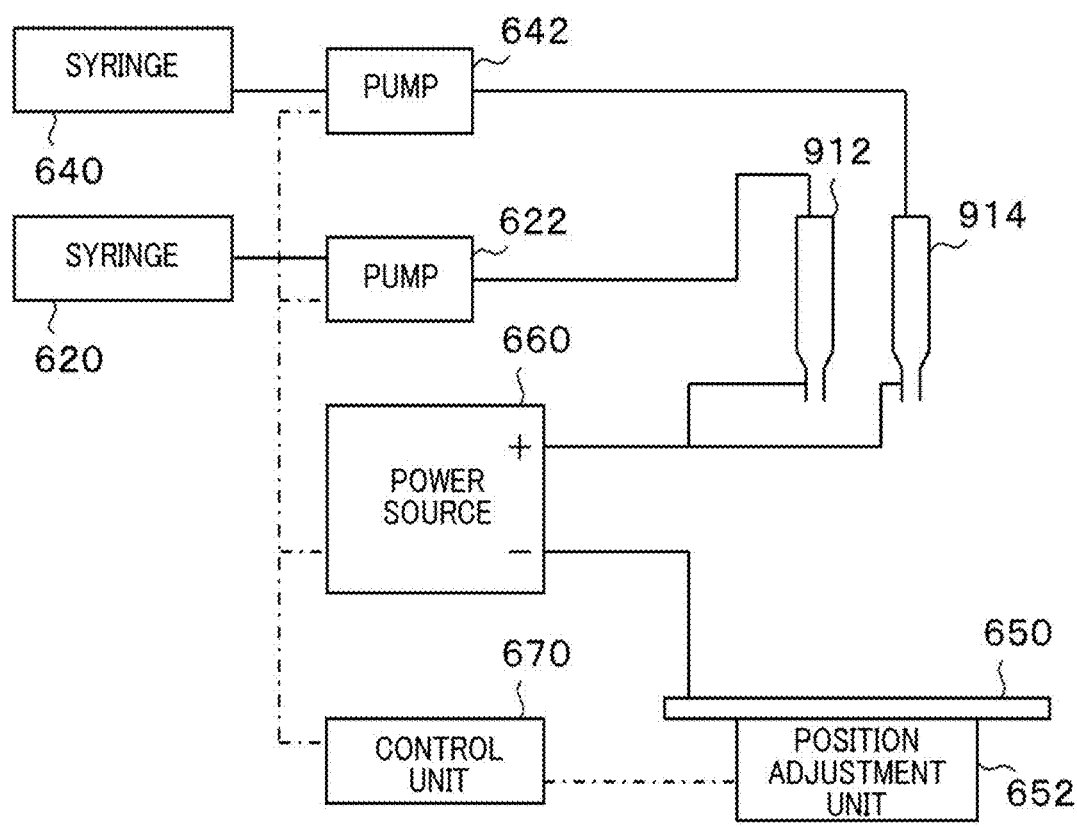
FIG. 9 schematically shows an example of a system configuration of an electrospinning system 900.

FIG. 9 schematically shows an example of a system configuration of an electrospinning system 900. The electrospinning system 900 is different from the electrospinning system 600 in that the electrospinning system 900 includes two single nozzles instead of the core shell nozzle 610. The single nozzle discharges, for example, liquid droplets that are not phase-separated. The electrospinning system 900 may have a configuration similar to that of the electrospinning system 600 except for the above described differences.

In the present embodiment, the first solution stored in the syringe 620 is supplied to a single nozzle 912 via the pump 622. The positive voltage is applied, by the power source 660, to the vicinity of a discharge outlet of the single nozzle 912. Thereby, the spinning jet of the first solution is ejected from the single nozzle 912 toward the collector plate 650.

In the present embodiment, the second solution stored in the syringe 640 is supplied to a single nozzle 914 via the pump 642. The positive voltage is applied, by the power source 660, to the vicinity of a discharge outlet of the single nozzle 914. Thereby, the spinning jet of the second solution is ejected from the single nozzle 914 toward the collector plate 650.

Figure 10:
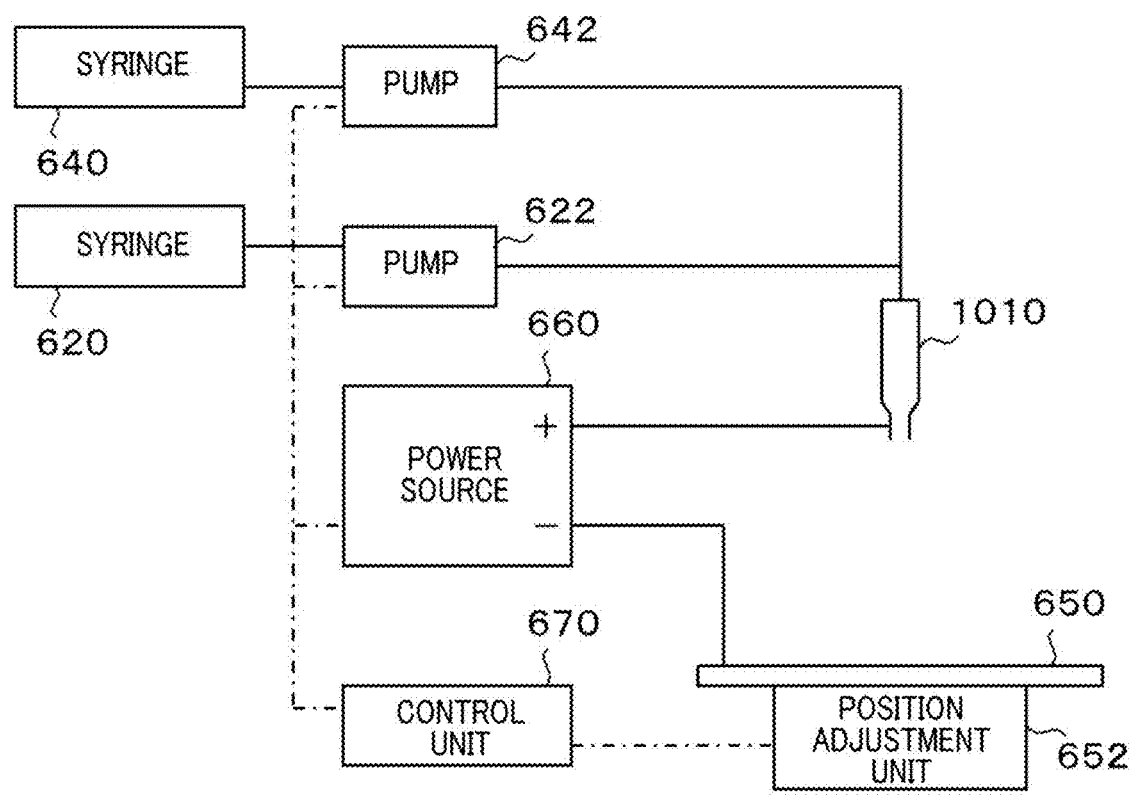
FIG. 10 schematically shows an example of a system configuration of an electrospinning system 1000.

FIG. 10 schematically shows an example of a system configuration of an electrospinning system 1000. The electrospinning system 1000 is different from the electrospinning system 600 in that the electrospinning system 1000 includes one single nozzle 1010 instead of the core shell nozzle 610 and that a spinning jet of a mixed solution of the first polymer material and the second polymer material is ejected. The electrospinning system 1000 may have a configuration similar to that of the electrospinning system 600 except for the above differences.

Figure 11:
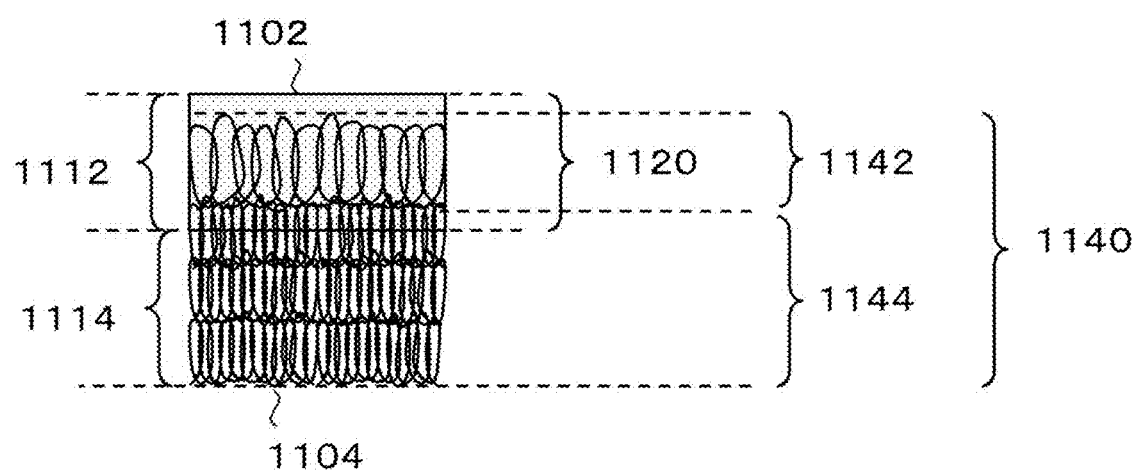
FIG. 11 schematically shows an example of a soft tissue repair material 1100.

FIG. 11 schematically shows an example of a soft tissue repair material 1100. In the present embodiment, the soft tissue repair material 1100 includes a monolith 1120 comprising the first polymer material, and a nonwoven fabric 1140 formed by aggregating fibers comprising the second polymer material. In the present embodiment, the nonwoven fabric 1140 has a sparse portion 1142 and a dense portion 1144. A bulk density of a fiber in the sparse portion 1142 is smaller than a bulk density of a fiber in the dense portion 1144. Further, a bulk density of the second polymer material in the sparse portion 1142 may be smaller than a bulk density of the second polymer material in the dense portion 1144.

In the present embodiment, the monolith 1120 is formed to cover the sparse portion 1142. The monolith 1120 may be formed to cover the sparse portion 1142, and a part of the dense portion 1144. A part of the monolith 1120 may enter pores of the nonwoven fabric 1140. The monolith 1120 is a porous body of a block shape, sponge shape, or a foam shape, and can be produced by any producing method. The monolith 1120 may be a porous body mainly consisting of the first polymer material, or may be a porous body comprising the first polymer material and the second polymer material.

In the present embodiment, a fiber constituting the nonwoven fabric 1140 may be a fiber of the second polymer material, and may be a composite fiber of the first polymer material and the second polymer material. A composition of the fiber constituting the sparse portion 1142 and a composition of the fiber constituting the dense portion 1144 may be the same, and may be different from each other. In one embodiment, one fiber constitutes a part of the sparse portion 1142, and a part of the dense portion 1144. In another embodiment, a web constituting the sparse portion 1142, and a web constituting the dense portion 1144 are integrated by any method.

In the present embodiment, the soft tissue repair material 1100 is divided into a surface layer region 1112 and a support layer region 1114 in the thickness direction. In the present embodiment, the surface layer region 1112 is arranged closer to a surface 1102 than the support layer region 1114 is. The surface layer region 1112 may be a region of the soft tissue repair material 1100 on the surface 1102 side, and the support layer region 1114 may be a region of the soft tissue repair material 1100 on a surface 1104 side.

As described above, in the present embodiment, the soft tissue repair material 1100 is a sheet shaped porous body having the surface 1102 and the surface 1104 opposite to each other. Further, the soft tissue repair material 1100 comprises the first polymer material and the second polymer material. As the first polymer material, for example, a material which has (i) a Young's modulus lower than that of the second polymer material and which has (ii) an in vivo disappearance rate, or absorbability with respect to the simulated biological fluid higher than that of the second polymer material is selected.

In the present embodiment, a composition in the surface layer region 1112, and a composition in the support layer region 1114 are different from each other. For example, (a) a ratio of a density of the second polymer material to a density of the first polymer material in the surface layer region 1112, and (b) a ratio of a density of the second polymer material to a density of the first polymer material in the support layer region 1114 are different from each other. The above described density may be an apparent density, and may be a bulk density.

More specifically, the ratio of the density of the second polymer material to the density of the first polymer material in the surface layer region 1112 may be smaller than the ratio of the density of the second polymer material to the density of the first polymer material in the support layer region 1114. When the soft tissue repair material 1100 is embedded in the living body, the monolith 1120 in the surface layer region 1112 functions as a scaffold for a biological tissue to regenerate in an initial stage of tissue regeneration. On the other hand, the nonwoven fabric 1140 remains in the living body for a longer period of time than the monolith 1120. Thereby, the strength of the soft tissue repair material 1100 is maintained until the biological tissue is sufficiently regenerated.

The soft tissue repair material 1100 may be an example of a porous body and a material for medical use. The surface 1102 may be an example of the first surface. The surface 1104 may be an example of the second surface. The surface layer region 1112 may be an example of the surface layer. The support layer region 1114 may be an example of the support layer. Note that the soft tissue repair material 1100 and its respective portions may have configurations similar to those of the soft tissue repair material 100, the soft tissue repair material 400, and their respective portions within a technically consistent range. Similarly, the soft tissue repair material 100, the soft tissue repair material 400, and their respective portions may have configurations similar to those of the soft tissue repair material 1100 and its respective portions within a technically consistent range.

Note that in the present embodiment, the soft tissue repair material 1100 has been described in detail by using, as an example, a case where the nonwoven fabric 1140 has the sparse portion 1142 and the dense portion 1144. However, the soft tissue repair material 1100 is not limited to the present embodiment. In another embodiment, a fiber density of the nonwoven fabric 1140 may be substantially uniform over the thickness direction of the nonwoven fabric 1140. In still another embodiment, a fiber density of the dense portion 1144 may change stepwise or continuously along the thickness direction of the dense portion 1144.

Figure 12:
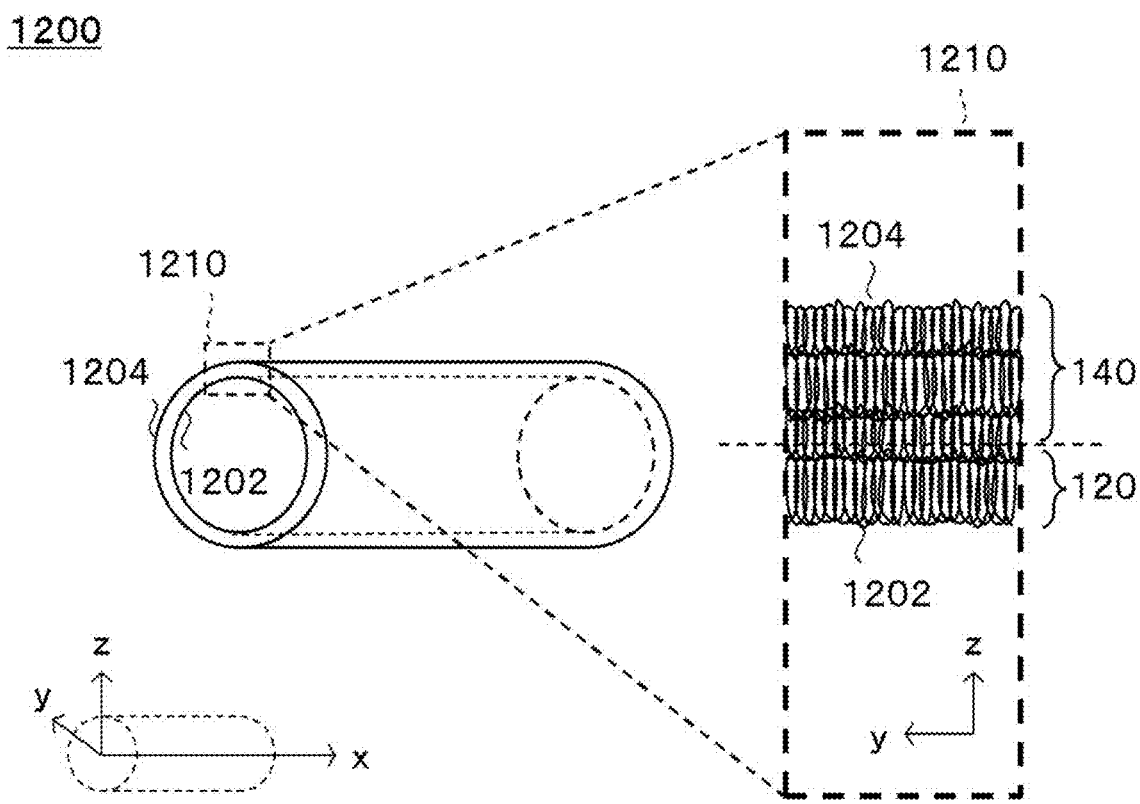
FIG. 12 schematically shows an example of a soft tissue repair material 1200.

FIG. 12 schematically shows an example of a soft tissue repair material 1200. FIG. 12 schematically shows an example of an enlarged view of a cross section of the soft tissue repair material 1200. In the present embodiment, the soft tissue repair material 1200 has a tube shape. The soft tissue repair material 1200 has an inner cavity surface 1202 and an outer cavity surface 1204. In the electrospinning system 600, the soft tissue repair material 1200 can be produced, for example, by using a rotating collector instead of the plate shaped collector plate 650.

The soft tissue repair material 1200 may be an example of a porous body and a material for medical use. The inner cavity surface 1202 may be an example of the first surface. The outer cavity surface 1204 may be an example of the second surface. Note that the soft tissue repair material 1200 and its respective portions may have configurations similar to those of the soft tissue repair material 100, the soft tissue repair material 400, the soft tissue repair material 1100, and their respective portions within a technically consistent range. Similarly, the soft tissue repair material 100, the soft tissue repair material 400, the soft tissue repair material 1100, and their respective portions may have configurations similar to those of the soft tissue repair material 1200 and its respective portions within a technically consistent range.

Figure 13:
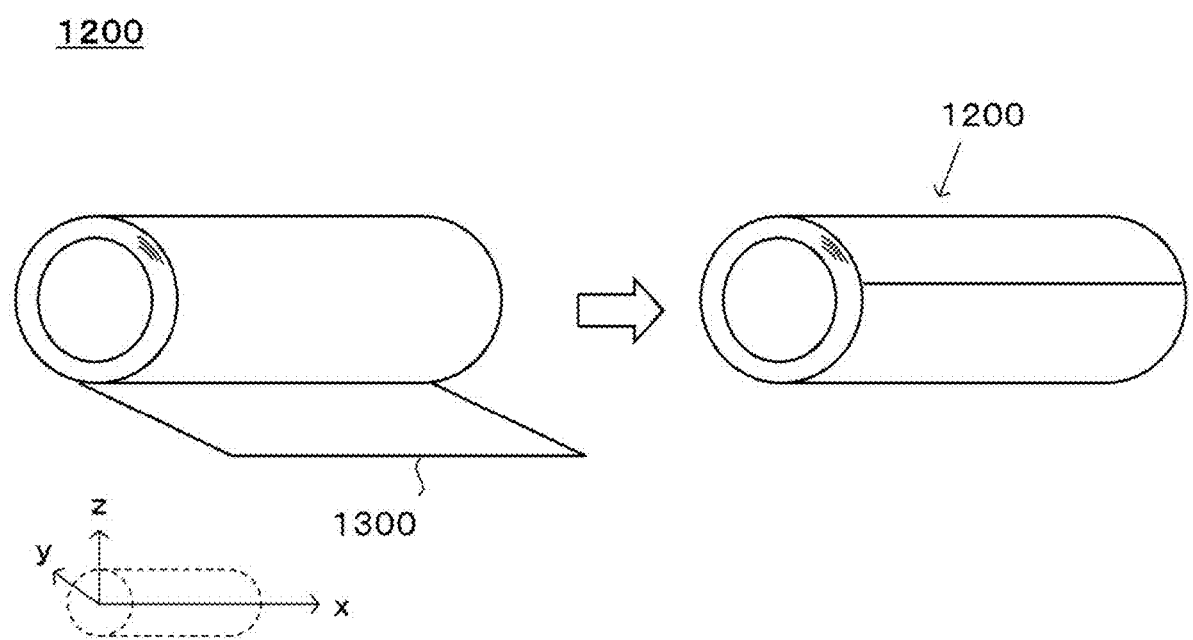
FIG. 13 schematically shows another example of a producing method for the soft tissue repair material 1200.

FIG. 13 schematically shows another example of a producing method for the soft tissue repair material 1200. In the present embodiment, the soft tissue repair material 1200 may be a rolled body of a sheet shaped material 1300. As shown in FIG. 13, the soft tissue repair material 1200 can be produced by winding the sheet shaped material 1300 multiple times to form a hollow rolled body. A plurality of layers constituting the hollow rolled body may be integrated by any method. The hollow rolled body may be cut in a plane substantially perpendicular to the extension direction to produce the soft tissue repair material 1200.

In one embodiment, the sheet shaped material 1300 may have a configuration similar to that of the soft tissue repair material 100 or the soft tissue repair material 400. In another embodiment, a composition of the sheet shaped material 1300 varies depending on a position in the x direction in the figure. For example, in the x direction of the sheet shaped material 1300, a content ratio of a specific component increases continuously or stepwise. In the x direction of the sheet shaped material 1300, the content ratio of the specific component may decrease continuously or stepwise. The specific component may be at least one of the first polymer material and the second polymer material. The sheet shaped material 1300 may have a substantially uniform composition distribution in the thickness direction.

Figure 14:
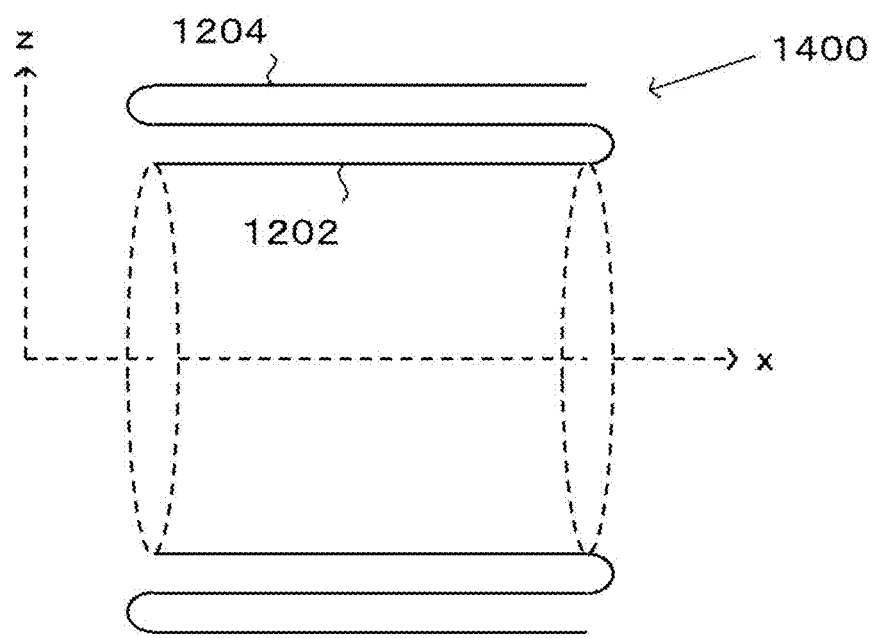
FIG. 14 schematically shows another example of the producing method for the soft tissue repair material 1200.

FIG. 14 schematically shows another example of the producing method for the soft tissue repair material 1200. In the present embodiment, the soft tissue repair material 1200 may be a cylinder-shaped woven fabric 1400. For example, cloth constituting the cylinder-shaped woven fabric 1400 is folded multiple times to form a plurality of layers in the radial direction (the z direction in the figure) of the cylinder-shaped woven fabric 1400. A plurality of layers constituting the cylinder-shaped woven fabric 1400 may be integrated by any method. The cylinder-shaped woven fabric 1400 may be cut in a plane substantially perpendicular to the extension direction to produce the soft tissue repair material 1200.

According to the present embodiment, at least two of the plurality of layers constituting the cylinder-shaped woven fabric 1400 may be layers which have compositions different from each other. For example, a composition of each layer is adjusted by adjusting at least one of a composition of a filament yarn constituting a warp yarn and a composition of a filament yarn constituting a weft yarn. The composition of the filament yarn constituting the warp yarn or the weft yarn is adjusted by, for example, a ratio of the number of filament yarns having a first composition, and the number of filament yarns having a second composition. The composition of the filament yarn is adjusted, for example, by compositions or combinations of a plurality of monofilaments constituting the filament yarn.

EXAMPLE

Hereinafter, the present invention will be described more specifically with reference to Example and Reference Examples. It should be noted that the present invention is not limited to the following Example unless the present invention goes beyond the gist.

<Specific Example Obtained by Using Polyvinyl Alcohol and Silk Fibroin>

Example 1

A nonwoven fabric shaped sheet was produced by the following procedure. In Example 1, polyvinyl alcohol (sometimes abbreviated as PVA) was used as the first polymer material, and silk fibroin was used as the second polymer material.

<Producing Silk Fibroin Sponge>

250 g of raw silk reeled from the domestic silkworm cocoon was immersed in an aqueous solution of 0.02 M sodium carbonate (a special grade reagent, manufactured by Wako Pure Chemical Industries, Ltd.) at 95° C., stirred for 30 minutes, and scoured. Then, the scoured raw silk was cleaned 5 times with purified water at 40° C. Thereby, sericin remaining in the scoured raw silk was almost completely removed. Subsequently, the fibers from which sericin had been removed were further cleaned with purified water, and then dried. Thereby, fibers of silk fibroin (sometimes abbreviated as SF) were obtained.

Then, the above described SF was added to an aqueous solution of 9M lithium bromide (manufactured by Wako Pure Chemical Industries, Ltd.), and the SF was dissolved under shaking conditions of 37° C. and 1000 rpm to obtain an SF solution. Subsequently, lithium bromide was removed from the SF solution by dialysis treatment. In the dialysis treatment, a dialysis cell tube boiled for 20 minutes was used. The dialysis treatment was performed under the condition of 4° C., and water was exchanged three times a day. The dialysis treatment was ended when an electric conductivity of the purified water became 2 μS/cm or less after 10 hours or more has passed after the water exchange.

Then, impurities were removed from the dialysis-treated SF aqueous solution by centrifugation. The centrifugation was carried out for 30 minutes under conditions of 4° C. and 8500 rpm. In addition, an operation of removing the impurities by the centrifugation was performed twice in total. Subsequently, a small amount of the SF aqueous solution from which the impurities had been removed was added dropwise to a plurality of petri dishes, and the weight after drying was measured to measure a concentration.

Then, the concentration of the SF aqueous solution was prepared to 1% (w/v). The SF aqueous solution having the prepared concentration was transferred to an eggplant flask, pre-frozen in liquid nitrogen, and then freeze-dried. Thereby, an SF sponge was obtained.

<Preparation of Silk Fibroin (SF) Solution>

After 120 g of SF sponge was added to 6000 μL of 1,1,1,3,3,3-hexafluoro-2-propanol (HFIP) (manufactured by Sigma), the mixture was stirred for 15 hours under conditions of room temperature and 300 rpm. Thereby, an HFIP solution of 2% (w/v) SF was obtained.

<Preparation of Polyvinyl Alcohol (PVA) Solution>

After 180 g of PVA (first grade, manufactured by Wako Pure Chemical Industries, Ltd.) was added to 6000 μL of 1,1,1,3,3,3-hexafluoro-2-propanol (HFIP) (manufactured by Sigma), the mixture was stirred overnight under conditions of room temperature and 300 rpm. Thereby, an HFIP solution of 3% (w/v) PVA was obtained.

<Producing Sheet Shaped NonWoven Fabric>

By using an electrospinning device (ES2000A, manufactured by Fuence Co., Ltd.), a fiber having a core-shell type of fiber structure in which an inside of the fiber is SF and an outside is PVA was produced. The ES2000A includes two syringes, and a core shell nozzle for producing a core-shell type of fiber, similarly to the electrospinning system 600 described with reference to FIG. 6. Table 1 shows conditions of the electrospinning process in Example 1.

TABLE 1

| Sample | Discharge rate [μl/min] SF-HFIP solution | Discharge rate [μl/min] PVA-HFIP solution | Discharge distance [cm] | Discharge time [hour] | Voltage [kV] | Nozzle Structure | The number of nozzle |
|---|---|---|---|---|---|---|---|
| Example 1 | 8 to 22 | 22 to 8 | 12 | 2 | 20 to 23 | core shell nozzle | 1 |
| Reference Example 1 | 8 | 22 | 12 | 2 | 20 to 23 | core shell nozzle | 1 |
| Reference Example 2 | 15 | 15 | 12 | 2 | 20 to 23 | core shell nozzle | 1 |
| Reference Example 3 | 22 | 8 | 12 | 2 | 20 to 23 | core shell nozzle | 1 |
| Reference Example 4 | 12 + 12 | — | 12 | 2.5 | 18 to 20 | single nozzle | 2 |

Specifically, first, one syringe of ES2000A was filled with the above described SF-HFIP solution, and the other syringe of ES2000A was filled with the above described PVA-HFIP solution. A discharge distance was set to 12 cm. Further, a discharge time was set to 2 hours. Subsequently, an applied voltage was set to 20 kV to 23 kV, and discharges of the SF-HFIP solution and the PVA-HFIP solution were started according to a previously programmed setting.

In Example 1, a discharge rate of the SF-HFIP solution was changed from 8 μl/min to 22 μl/min during the discharge time of 2 hours. Specifically, the discharge rate of the SF-HFIP solution was increased stepwise by 1 μl/min every 8 minutes. In addition, a discharge rate of the PVA-HFIP solution was changed from 22 μl/min to 8 μl/min. Specifically, the discharge rate of the PVA-HFIP solution was decreased stepwise by 1 μl/min every 8 minutes. Thereby, a nonwoven fabric shaped sheet was produced on a collector plate made of aluminum. A size of the above described sheet was 50 mm×50 mm. Note that in an evaluation of the sheet, a surface on a side in contact with the collector plate may be referred to as a rear surface, and a surface on the opposite side of the rear surface may be referred to as a front surface.

Then, the produced sheet was allowed to sit for 24 hours together with the collector plate under conditions of a relative humidity of 100%, and 37° C. so as to insolubilize silk fibroin. Subsequently, the insolubilized sheet was immersed in water together with the collector plate, and the sheet was peeled off from the collector plate. The sheet peeling operation was carried out within 5 minutes. This made it possible to peel off the sheet from the collector plate while dissolution of PVA was suppressed.

Reference Example 1

In the electrospinning process, the nonwoven fabric shaped sheet was produced by a procedure similar to that in Example 1 except that the discharge rate of the SF-HFIP solution was fixed at 8 μl/min and the discharge rate of the PVA-HFIP solution was fixed at 22 μl/min. Table 1 shows conditions of the electrospinning process in Reference Example 1.

Reference Example 2

In the electrospinning process, the nonwoven fabric shaped sheet was produced by a procedure similar to that in Example 1 except that the discharge rate of the SF-HFIP solution was fixed at 15 μl/min and the discharge rate of the PVA-HFIP solution was fixed at 15 μl/min. Table 1 shows conditions of the electrospinning process in Reference Example 2.

Reference Example 3

In the electrospinning process, the nonwoven fabric shaped sheet was produced by a procedure similar to that in Example 1 except that the discharge rate of the SF-HFIP solution was fixed at 22 μl/min and the discharge rate of the PVA-HFIP solution was fixed at 8 μl/min. Table 1 shows conditions of the electrospinning process in Reference Example 3.

Reference Example 4

Similarly to the electrospinning system 900 described with reference to FIG. 9, instead of using one core shell nozzle in the electrospinning device (ES2000A, manufactured by Fuence Co., Ltd.), the nonwoven fabric shaped sheet was produced by using two single nozzles. Table 1 shows conditions of the electrospinning process in Reference Example 4.

Specifically, first, one syringe of ES2000A was filled with the above described SF-HFIP solution, and the other syringe of ES2000A as well was filled with the above described SF-HFIP solution. The discharge distance was set to 12 cm. In addition, the discharge time was set to 2.5 hours. Subsequently, the applied voltage was set to 20 kV to 23 kV, and discharges of the SF-HFIP solution and the PVA-HFIP solution were started according to the previously programmed setting. Specifically, during the discharge time of 2.5 hours, the discharge rate of the SF-HFIP solution from the one syringe was fixed at 12 μl/min, and the discharge rate of the SF-HFIP solution from the other syringe was also fixed at 12 μl/min. Other procedures were carried out in a manner similar to that in Example 1.

[Evaluation Method]

The sheets of Example 1 and Reference Examples 1 to 4 were evaluated by the following procedure. Specifically, a form, a composition, physical properties and degradability of each sheet were evaluated.

<Morphological Observation>

A test piece was collected from each sheet, each test piece was gold vapor-deposited, and then a surface of each test piece was observed by using a scanning electron microscope (JSM-6510, manufactured by JEOL Ltd.). An observation voltage of the scanning electron microscope was set to 10 kV, and magnification was set to 3000 times. The test piece was collected from the center portion of each sheet. The test piece had a size of a circle with a diameter of 4 mm. In addition, an image J (Ver 1.51j8, manufactured by National Institutes of Health (NIH)) was used to analyze an image obtained by the scanning electron microscope. Specifically, an average fiber diameter of fibers existing on the surface of each sheet was calculated. The average fiber diameter of the fibers was calculated by the following procedure. First, at least 50 fibers were randomly extracted from among the SEM image of each sheet. Then, fiber diameters of the respective extracted fibers were determined. Subsequently, an average value of the determined fiber diameters of the respective fibers was calculated.

<Composition Evaluation>

(ATR-FTIR Measurement)

For the sheets (Example 1 and Reference Examples 1 to 3) formed of the fiber having a core-shell structure, FT-IR measurements (sometimes referred to as ATR-FTIR measurements) by a total reflection method (ATR method) were carried out. The ATR-FTIR measurement was carried out by using an FT/IR-4600 Fourier transform infrared spectrophotometer manufactured by JASCO Corporation. The ATR-FTIR measurement was carried out on the front surface and the rear surface of Example 1, and front surfaces of Reference Examples 1 to 3. For measurement conditions of the ATR-FTIR measurement, the cumulative number was set to 16 times, and a measurement range was set to 900 $cm^{-1}$ to 1800 $cm^{-1}$. For a prism, ZnSe was used. A spectrum obtained by measuring each observation target was normalized by a peak of amide I derived from SF appearing in a range of 1650 $cm^{-1}$ to 1630 $cm^{-1}$. In the normalized spectrum, the peak intensities of C—O stretching vibrations derived from PVA appearing at 1095 $cm^{-1}$ were compared. Thereby, in the sheet of Example 1, it was confirmed that abundance ratios of SF and PVA were changed in the thickness direction.

(NMR Measurement)

NMR measurements were carried out on the sheets of Reference Examples 1 to 4. The NMR measurement was carried out by using ECX-500 manufactured by JEOL Ltd. Specifically, 3 mg of sample was collected from a surface in the vicinity of the center of each sheet on a surface side. The sample collected from among each sheet was dissolved in 0.6 ml of a deuterated solvent for the NMR measurement (for NMR, manufactured by Kanto Chemical Co., Inc.), and transferred to an NMR tube having a diameter of 5 mm. The NMR tube of each sample was set in an NMR measurement device, and $^1$H-NMR was measured. For each sample, by calculating a ratio of a peak area of an alanine side chain methyl group of SF, and a peak area of a methylene group of PVA, a mass ratio of SF and PVA in the sample was calculated.

<Physical Property Evaluation>

First, each insolubilized sheet was immersed in purified water to be in a water containing state. Then, a 15 mm×3 mm test piece was cut out from each sheet. In addition, a film thickness of the test piece was measured. Then, tensile testing in water was carried out by using a 100 N load cell of MICROTEST200N Tensile Stage (manufactured by Deben UK Ltd.). The tensile testing in water was carried out in water at 37° C. with a length between grips being 5 mm, and a tensile speed being 0.5 mm/min. The number of times of measurement trials was at least eight. A stress [Pa] and a strain [%] were calculated based on a test force [N], a displacement [mm], a film thickness [mm], and a sample length [mm] obtained by the tensile testing in water. A stress-strain curve (Stress-Strain curve) was produced by plotting the measurement results with the vertical axis representing the stress and the horizontal axis representing the strain. A Young's modulus was calculated based on the stress for the strain of 1% to 4%.

<Degradability Evaluation>

By using the sheets obtained in each of Reference Examples 1 to 3, a test on absorbability with respect to a simulated biological fluid (sometimes referred to as degradability testing) was carried out. Specifically, first, a 1 cm×1 cm test piece was cut out from each sheet. Each of the cut out test pieces was vacuum-dried to sufficiently remove water of each test piece, and then a mass of each test piece was measured. Then, each test piece was inserted into an Eppendorf tube containing 1.2 mL of phosphate buffered saline (Calbiochem), and allowed to sit for 7 days. A composition of PBS is 200 mg/L of potassium dihydrogen phosphate, 200 mg/L of potassium chloride, 1150 mg/L of disodium hydrogen phosphate, and 8000 mg/L of sodium chloride. A temperature of PBS was maintained at 37° C. In addition, PBS was exchanged every two days.

After the immersion treatment in PBS was ended, each test piece was taken from the Eppendorf tube, and each test piece was cleaned with purified water. Subsequently, each test piece was vacuum-dried to sufficiently remove water of each test piece, and then a mass of each test piece was measured. A mass loss rate [%] was calculated based on mass measurement results before and after the immersion treatment in PBS. The mass loss rate [%] was calculated based on the following Mathematical Expression 3.

$$\text{Mass loss rate [\%]}=100\times(\text{a mass before the test starts}-\text{a mass when the test ends})/\text{the mass before the test starts.} \qquad [\text{Math. 3}]$$

In addition, each test piece for which the degradability testing had been ended was gold vapor-deposited, and then a surface of each test piece was observed by using a scanning electron microscope (JSM-6510, manufactured by JEOL Ltd.). An observation voltage of the scanning electron microscope was set to 10 kV, and magnification was set to 3000 times.

[Evaluation Result]

<Result of Morphological Observation>

Figure 15:
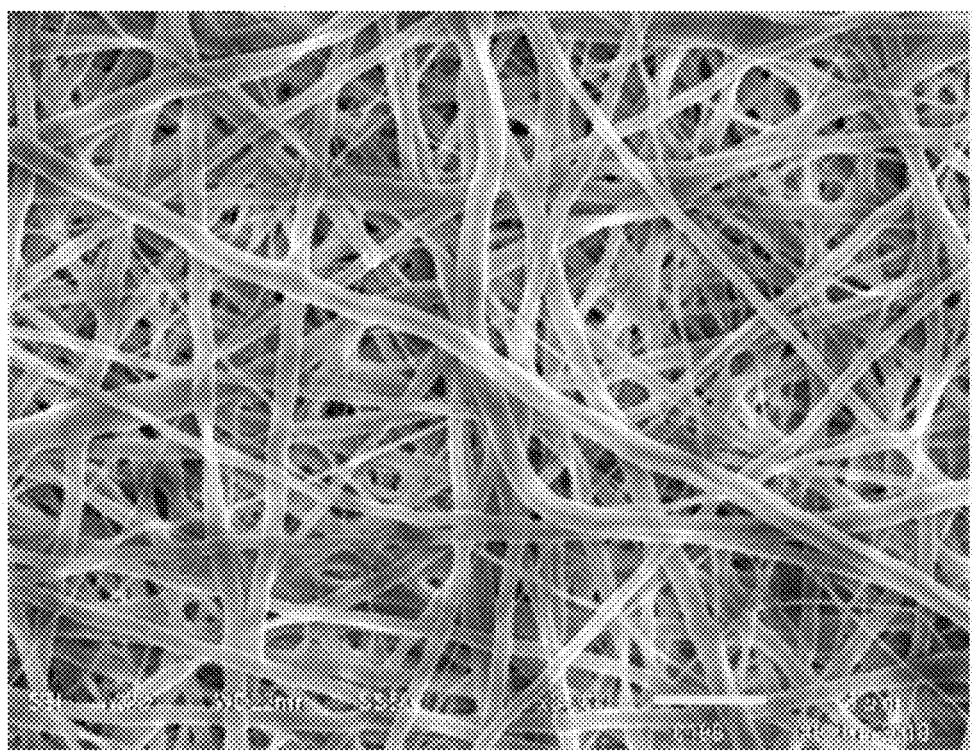
FIG. 15 shows an SEM image of an appearance in Reference Example 1.
Figure 16:
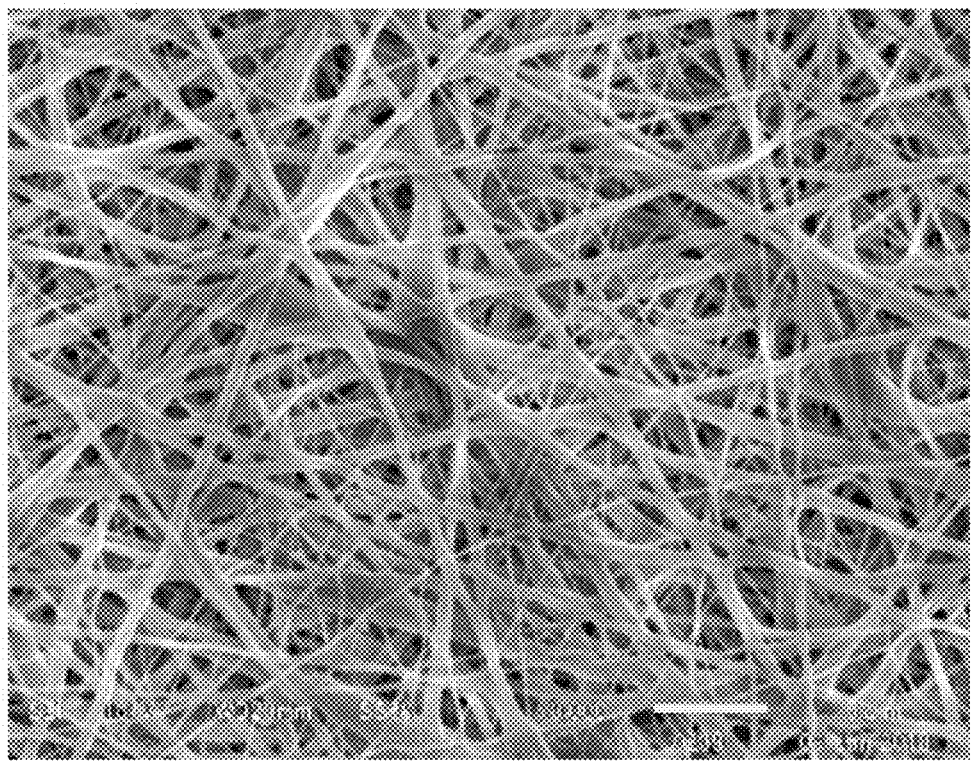
FIG. 16 shows an SEM image of an appearance in Reference Example 2.
Figure 17:
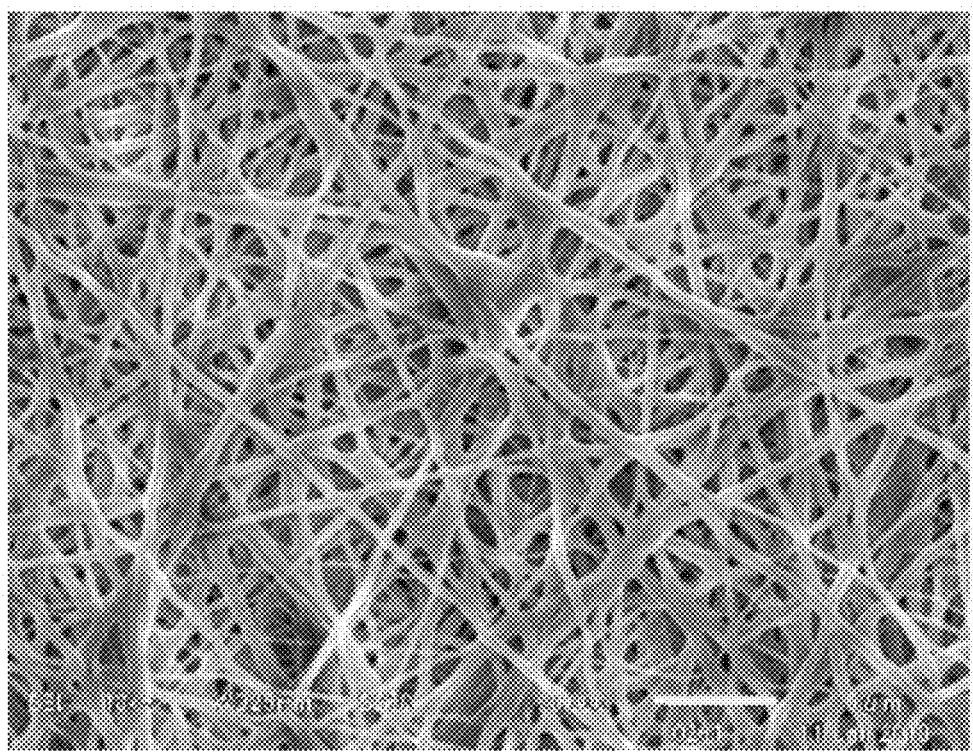
FIG. 17 shows an SEM image of an appearance in Reference Example 3.
Figure 18:
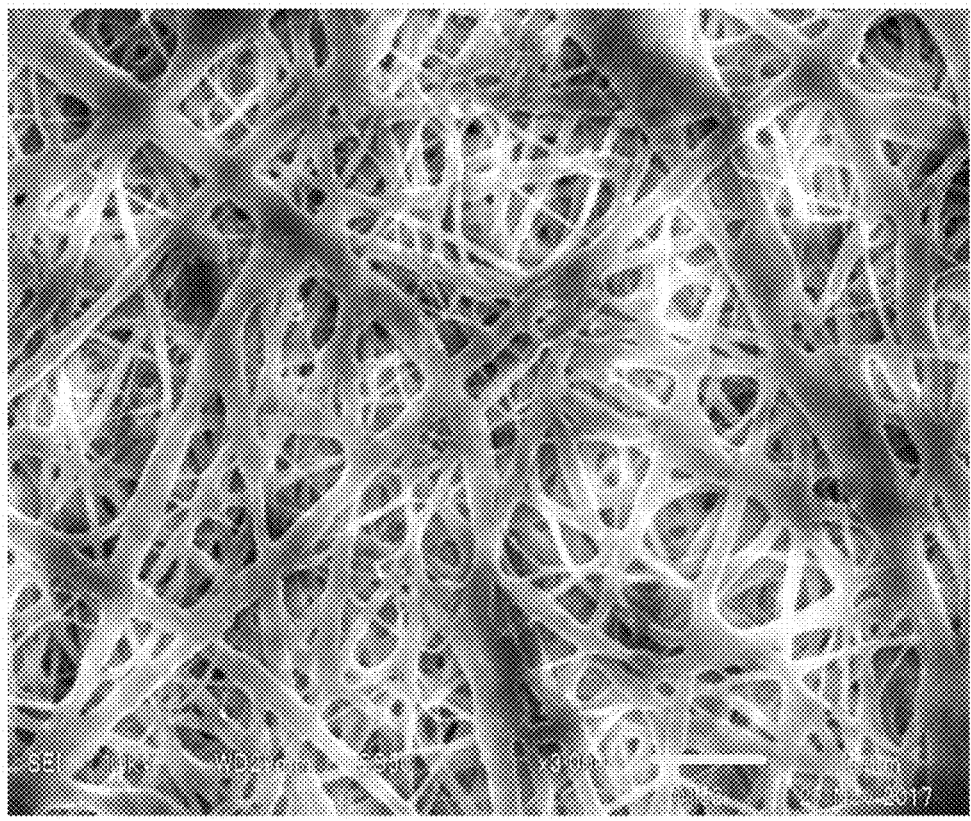
FIG. 18 shows an SEM image of an appearance in Example 1.
Figure 19:
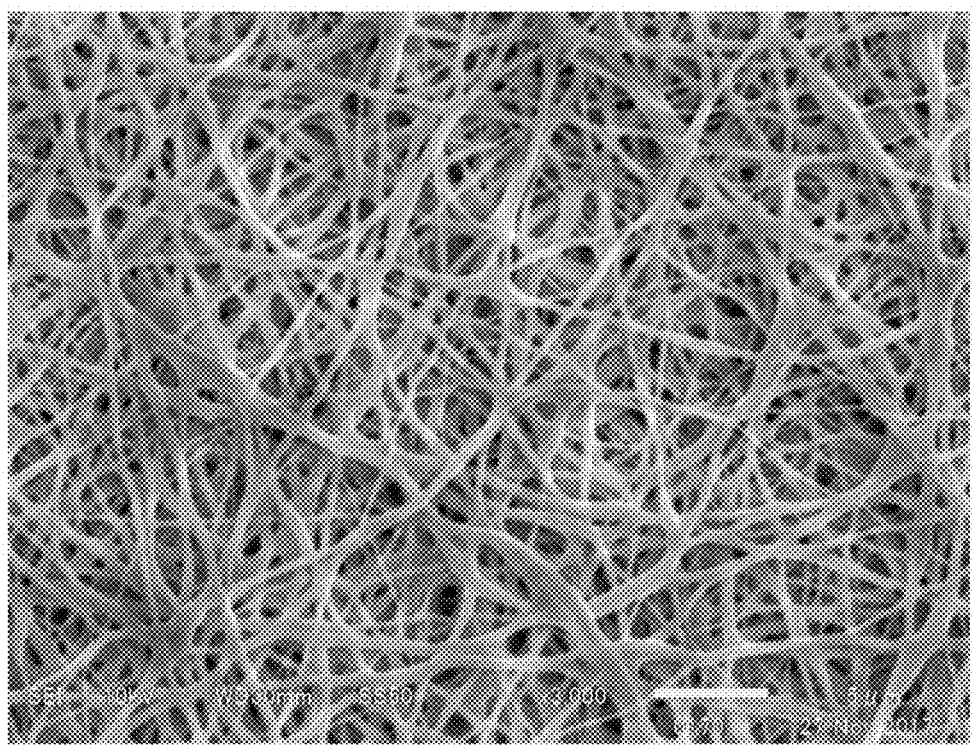
FIG. 19 shows an SEM image of an appearance in Example 1.
Figure 20:
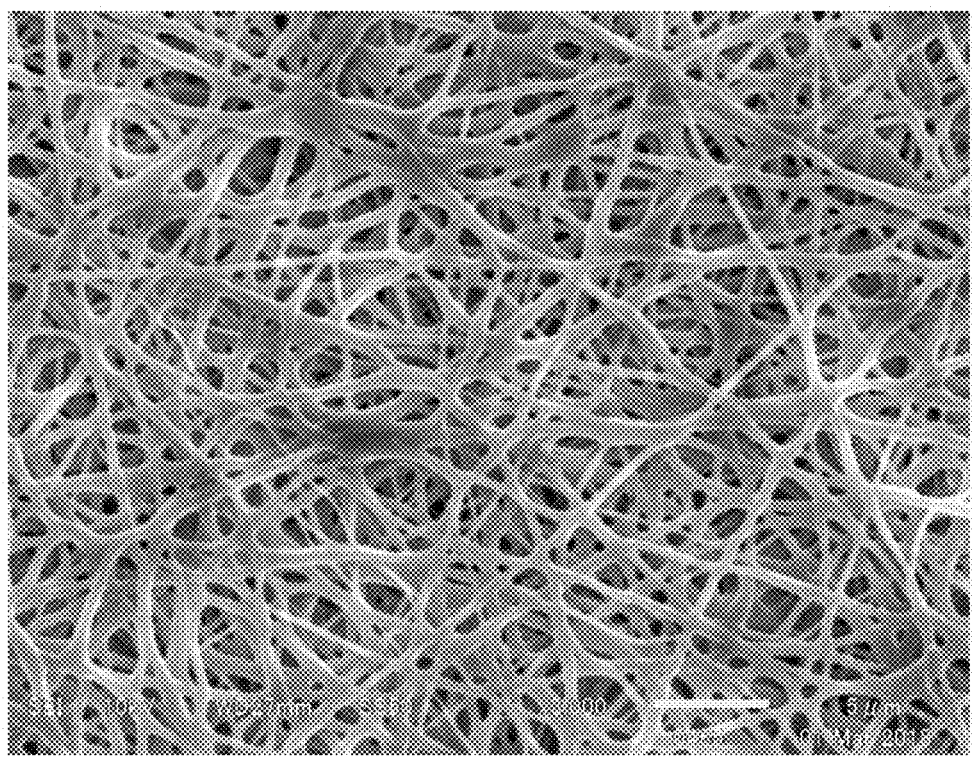
FIG. 20 shows an SEM image of an appearance in Reference Example 4.

FIG. 15 to FIG. 20 show SEM images of appearances of Example 1 and Reference Examples 1 to 4. FIG. 15 shows an SEM image of the front surface of Reference Example 1. FIG. 16 shows an SEM image of the front surface of Reference Example 2. FIG. 17 shows an SEM image of the front surface of Reference Example 3. FIG. 18 shows an SEM image of the rear surface of Example 1. FIG. 19 shows an SEM image of the front surface of Example 1. FIG. 20 shows an SEM image of the front surface of Reference Example 4. Further, Table 2 shows an average fiber diameter of each sample.

TABLE 2

| Sample | Average fiber diameter [μm] |
| --- | --- |
| Example 1 | Side where producing started: 0.60.22<br>Side where producing is ended: 0.393 ± 0.119 |
| Reference Example 1 | 0.675 ± 0.218 |
| Reference Example 2 | 0.597 ± 0.188 |
| Reference Example 3 | 0.435 ± 0.103 |
| Reference Example 4 | 0.393 ± 0.117 |

As shown in FIG. 15 to FIG. 20, formations of the fiber structures were confirmed in all the samples. Note that as shown in Table 2, as the discharge rate of PVA increased, the average fiber diameter increased. In electrospinning, it has been reported that the larger the viscosity of the solution, the larger the fiber diameter. Since the viscosity of the PVA solution was higher than the viscosity of the SF solution, it is presumed that as the discharge rate of PVA increased, the average fiber diameter increased.

According to FIG. 18 and FIG. 19, the average fiber diameter of the rear surface of the sheet of Example 1 is greater than the average fiber diameter of the front surface. Based on the above described presumption, it is presumed that in Example 1, the fiber on the rear surface of the sheet has a relatively great PVA content, and the fiber on the front surface of the sheet has a relatively great SF content.

Figure 26:
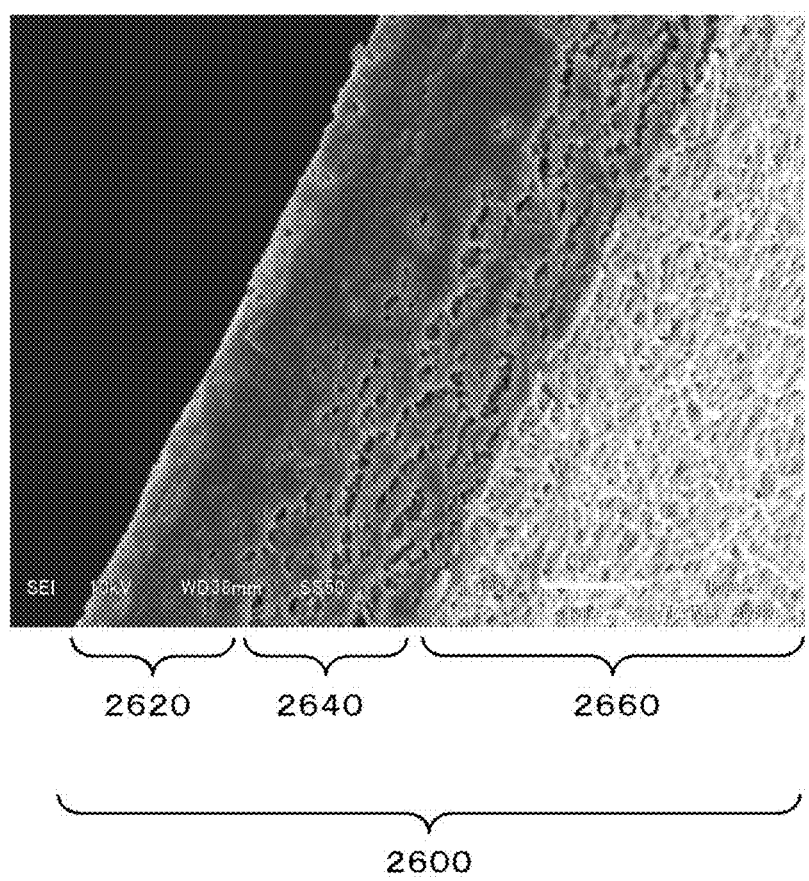
FIG. 26 shows an SEM image of a cross section of Example 1 in the thickness direction.

FIG. 26 shows an SEM image of a cross section of a sheet 2600 of Example 1 in the thickness direction. As shown in FIG. 26, in order from a rear surface side of the sheet 2600, the sheet 2600 has a layer 2620 of a PVA-rich fiber, a layer 2640 of a fiber having a greater silk content than that of a fiber constituting a layer 2660, and the layer 2660 of a silk-rich fiber. As shown in FIG. 26, in the sheet 2600, a bulk density of the fiber in the layer 2620 is higher than a bulk density of the fiber in the layer 2660.

Note that in the present embodiment, inside the layer 2620 as well, a component ratio of PVA and silk fibroin is changed stepwise along the direction from the rear surface toward the front surface. Similarly, inside the layer 2640 and the layer 2660 as well, component ratios of PVA and silk fibroin are changed stepwise along the direction from the rear surface toward the front surface.

<Composition Evaluation>

Figure 21:
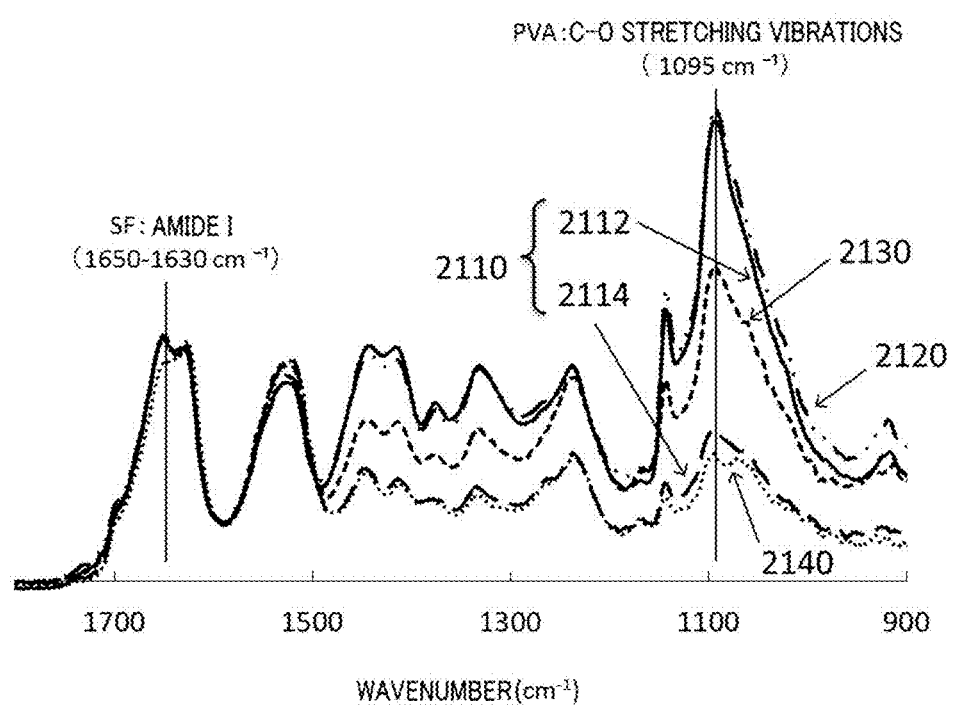
FIG. 21 shows ATR-FTIR measurement results of Example 1 and Reference Examples 1 to 3.

FIG. 21 shows ATR-FTIR measurement results of Example 1 and Reference Examples 1 to 3. In FIG. 21, a curve 2110 shows a measurement result of Example 1. A curve 2112 shows a measurement result of the rear surface of the sheet of Example 1. A curve 2114 shows a measurement result of the front surface of the sheet of Example 1. A curve 2120 shows a measurement result of Reference Example 1. A curve 2130 shows a measurement result of Reference Example 2. A curve 2140 shows a measurement result of Reference Example 3.

As shown in FIG. 21, as the discharge rate of PVA increased, a peak intensity of C—O stretching vibration derived from PVA increased. This makes it possible to confirm that as the discharge rate of PVA increases, the PVA content in the fiber also increases. Further, in FIG. 21, the curve 2112 and the curve 2120 match well each other, and the curve 2114 and the curve 2140 match well each other. Thereby, it is presumed that the abundance ratios of SF and PVA in the sheet of Example 1 are changed stepwise in the thickness direction thereof.

Further, according to the results of the NMR measurement of Reference Examples 1 to 4, SF:PVA in Reference Example 1, Reference Example 2, and Reference Example 3 were 8:23, 15:13, and 22:7, in mass ratio, respectively. This shows that a mass ratio of the discharge rates of the SF solution and the PVA solution can be regarded as a mass ratio of SF and PVA in the sheet.

<Result of Physical Property Evaluation>

Figure 22:
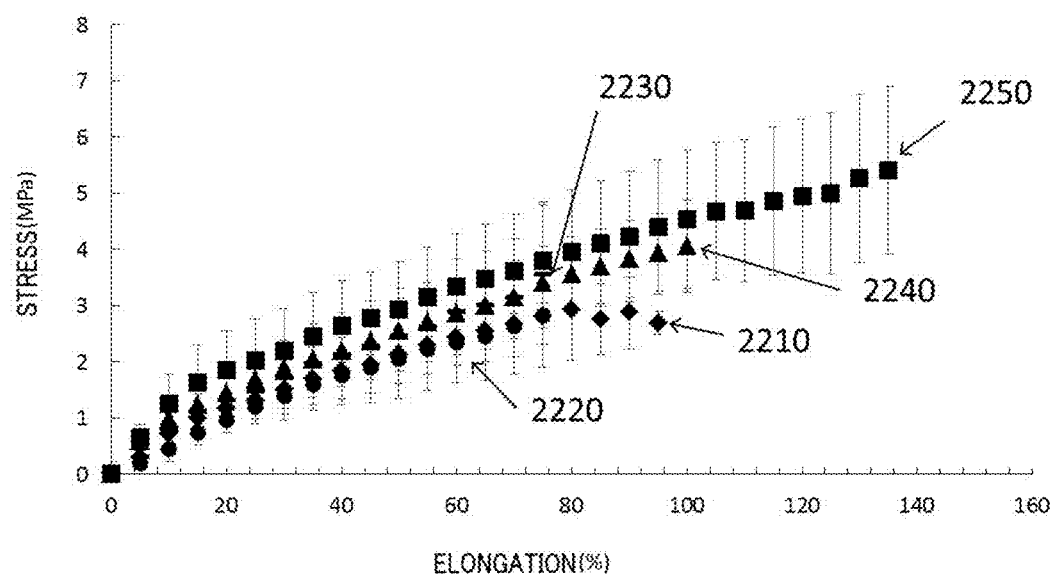
FIG. 22 shows tensile testing results of Example 1 and Reference Examples 1 to 4.

FIG. 22 shows tensile testing results of Example 1 and Reference Examples 1 to 4. In FIG. 22, a curve 2210 of a diamond shaped marker shows a measurement result of Example 1. A curve 2220 of a round marker shows a measurement result of Reference Example 1. A curve 2230 of a horizontal bar type marker shows a measurement result of Reference Example 2. A curve 2240 of a triangular marker shows a measurement result of Reference Example 3. A curve 2250 of a quadrangular marker shows a measurement result of Reference Example 4. Further, Table 3 shows a measurement result of a Young's modulus of each sample. As shown in FIG. 22 and Table 3, as the discharge rate of PVA increased, the Young's modulus decreased. This makes it possible to confirm that as the discharge rate of PVA increases, a flexibility of the fiber improves. In addition, the Young's modulus of the sheet of Example 1 decreased significantly in comparison with that of the sheet of Reference Example 4.

TABLE 3

| Sample | Film thickness [μm] | | Young's modulus [MPa] | | |
|---|---|---|---|---|---|
| | Dry state | Water containing state | Average | Maximum | Minimum |
| Example 1 | 55 ± 10.4 | 75 ± 11.2 | 6.1 ± 3.8 | 12.75 | 2.67 |
| Reference Example 1 | 52 ± 8 | 97 ± 2.5 | 3.5 ± 1.1 | 5.48 | 2.27 |
| Reference Example 2 | 62 ± 7.1 | 63 ± 5.6 | 5.8 ± 1.4 | 7.90 | 3.63 |
| Reference Example 3 | 61 ± 6.5 | 91 ± 8.7 | 11.4 ± 2.3 | 14.22 | 8.65 |
| Reference Example 4 | 50 ± 9 | 55 ± 2.5 | 14.5 ± 2.3 | 20.74 | 8.63 |

A Young's modulus of a blood vessel varies to some extent depending on a site; however, the Young's modulus of the human artery is about 0.4 MPa to 1.8 MPa. On the other hand, it has been reported that an elastic modulus of expanded polytetrafluoroethylene (ePTFE) which is currently used widely as an artificial blood vessel is approximately 20 MPa. Accordingly, it can be seen that the sheet of Example 1 shows a lower Young's modulus than that of the existing artificial blood vessel and has physical properties closer to those of the human artery in Young's modulus.

<Degradability Evaluation>

Figure 23:
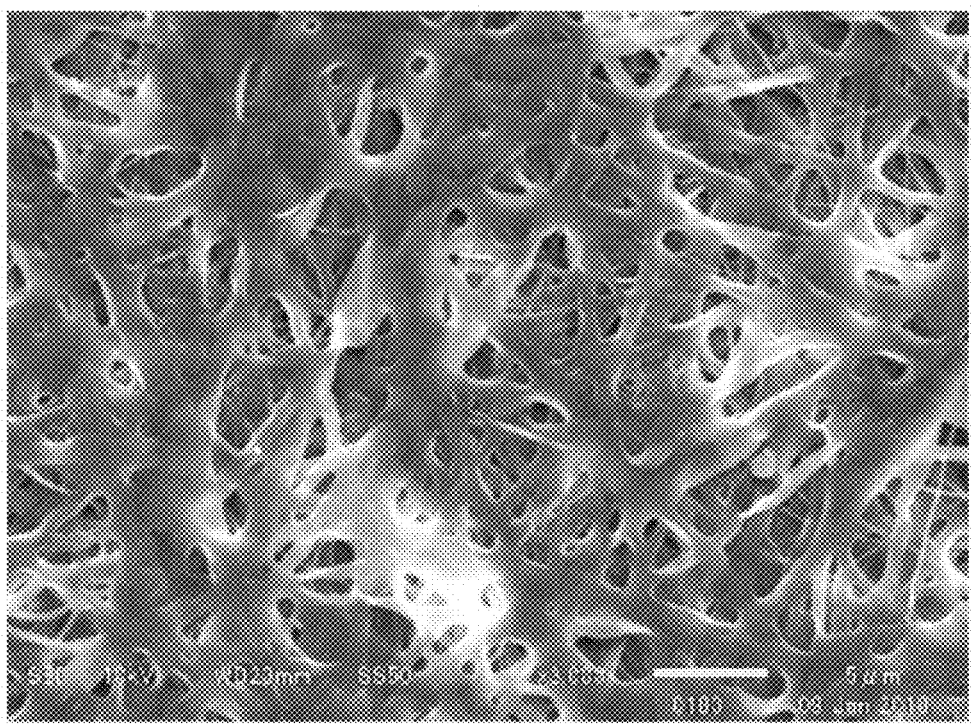
FIG. 23 shows an SEM image of an appearance in Reference Example 1 after an end of degradability testing.
Figure 24:
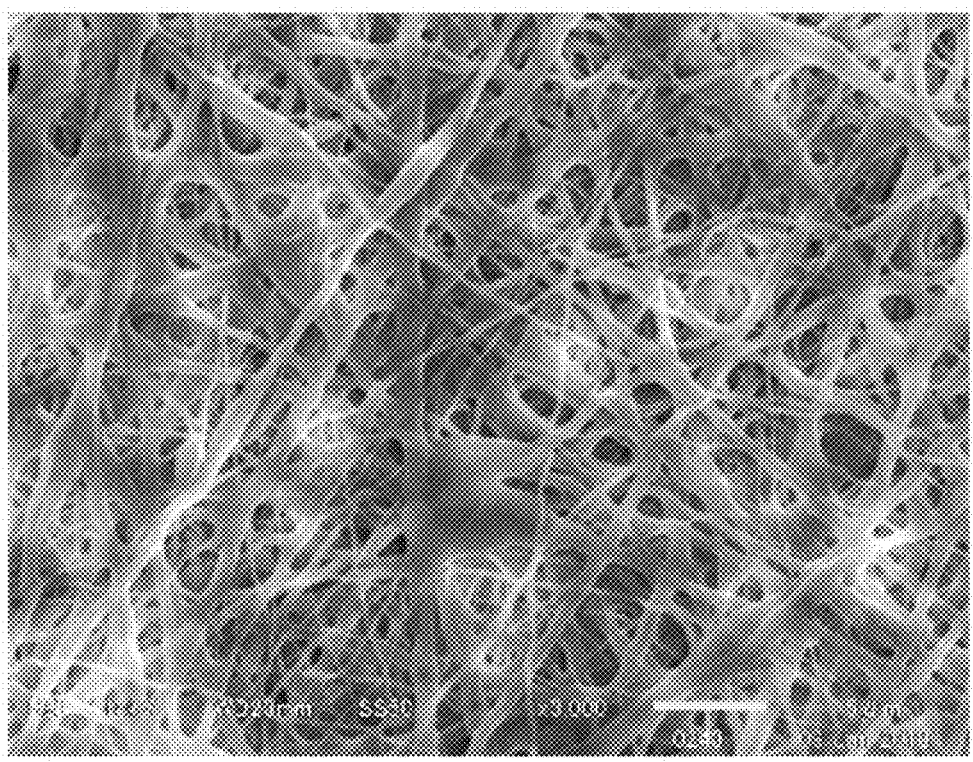
FIG. 24 shows an SEM image of an appearance in Reference Example 2 after an end of degradability testing.
Figure 25:
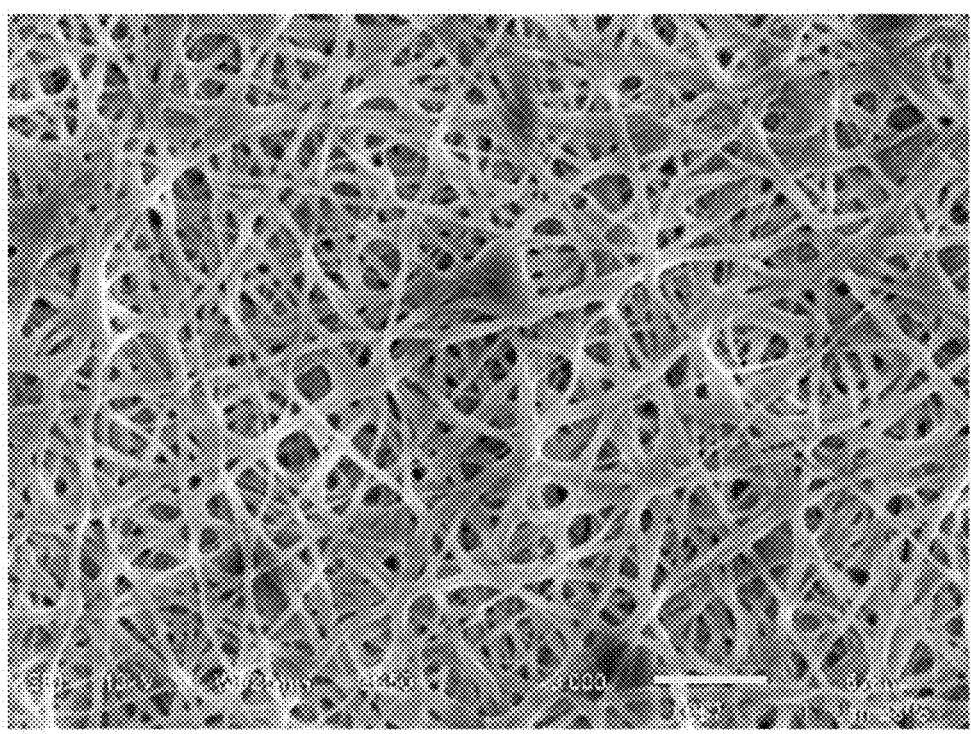
FIG. 25 shows an SEM image of an appearance in Reference Example 3 after an end of degradability testing.

Table 4 shows a mass loss rate in the degradability evaluation test of Reference Examples 1 to 3. Further, FIG. 23 shows an SEM image of an appearance in Reference Example 1 after an end of degradability testing. FIG. 24 shows an SEM image of an appearance in Reference Example 2 after an end of degradability testing. FIG. 25 shows an SEM image of an appearance in Reference Example 3 after an end of degradability testing.

TABLE 4

| | Mass loss rate [%] | | |
|---|---|---|---|
| Sample | Average | Maximum | Minimum |
| Reference Example 1 | 20 ± 1.7 | 21.88 | 18.75 |
| Reference Example 2 | 13.5 ± 2.2 | 16.67 | 11.43 |
| Reference Example 3 | 4.6 ± 0.3 | 4.88 | 4.26 |

As shown in Table 4, as the discharge rate of PVA decreased, the mass loss rate decreased. Thereby, it can be seen that by changing the abundance ratios of SF and PVA in the thickness direction thereof, it is possible to produce, as the sheet of Example 1, a sheet in which the degradation or the absorption progresses from one side of the sheet into the living body.

As shown in FIG. 23, film formation of the sheet of Reference Example 1 was confirmed. As shown in FIG. 24, dissolution of the fibers was confirmed in a part of the sheet of Reference Example 2. On the other hand, as shown in FIG. 25, in the sheet of Reference Example 3, the film formation and the dissolution of the fiber were not confirmed. It is presumed that as an amount of PVA in the fiber increased, the film formation of the sheet or the dissolution of the fiber progressed.

<Specific Example Obtained by Using Collagen and Silk Fibroin>

Reference Example 51

A nonwoven fabric shaped sheet was produced by the following procedure. In Reference Example 5, atelocollagen (sometimes abbreviated as collagen) was used as the first polymer material, and silk fibroin was used as the second polymer material.

<Preparation of Silk Fibroin (SF) Solution>

By a procedure similar to that in Example 1, after 180 g of SF sponge was added to 6000 μL of 1,1,1,3,3,3-hexafluoro-2-propanol (HFIP) (manufactured by Sigma), the mixture was stirred for 15 hours under conditions of room temperature and 300 rpm. Thereby, an HFIP solution of 3% (w/v) SF was obtained.

<Preparation of Atelocollagen Solution>

Similarly, after 240 g of atelocollagen (a manufacturer, a product number, or the like) was added to 6000 μL of 1,1,1,3,3,3-hexafluoro-2-propanol (HFIP) (manufactured by Sigma), the mixture was stirred overnight under conditions of room temperature and 300 rpm. Thereby, an HFIP solution of 4% (w/v) atelocollagen was obtained.

<Producing Sheet Shaped Nonwoven Fabric>

By using the electrospinning device (ES2000A, manufactured by Fuence Co., Ltd.), a fiber having a core-shell type of fiber structure in which an inside of the fiber is SF and an outside is atelocollagen was produced. Specifically, in the electrospinning process, the nonwoven fabric shaped sheet was produced by a procedure similar to that in Example 1 except that the discharge rate of the SF-HFIP solution was fixed at 15 μl/min, the discharge rate of the collagen-HFIP solution was fixed at 15 μl/min, the discharge time was set to 4 minutes, and the applied voltage was set to 22V. Table 5 shows conditions of the electrospinning process in Reference Example 5.

TABLE 5

| Sample | Discharge rate [μl/min] | | Discharge distance [cm] | Discharge time [hour] | Voltage [kV] | Nozzle Structure | The number of nozzle |
| --- | --- | --- | --- | --- | --- | --- | --- |
| | SF-HFIP solution | Collagen-HFIP solution | | | | | |
| Reference Example 5 | 15 | 15 | 12 | 4 | 22 | Core shell nozzle | 1 |
| Reference Example 6 | 15 | 15 | 12 | 4 | 24 | Core shell nozzle | 1 |
| Reference Example 7 | 8 | 22 | 12 | 4 | 24 | Core shell nozzle | 1 |

Reference Example 6

In the electrospinning process, the nonwoven fabric shaped sheet was produced by a procedure similar to that in Reference Example 5 except that the applied voltage was set to 24V. Table 5 shows conditions of the electrospinning process in Reference Example 6.

Reference Example 7

In the electrospinning process, the nonwoven fabric shaped sheet was produced by a procedure similar to that in Reference Example 6 except that the discharge rate of the SF-HFIP solution was fixed at 8 μl/min and the discharge rate of the collagen-HFIP solution was fixed at 22 μl/min. Table 5 shows conditions of the electrospinning process in Reference Example 7.

<Result of Morphological Observation>

Figure 27:
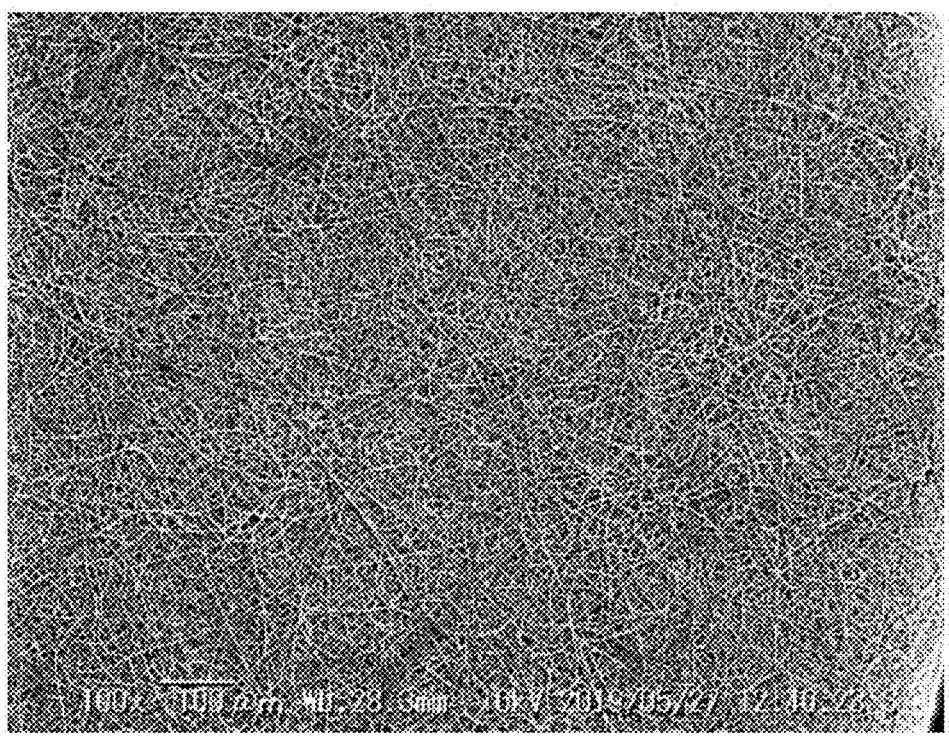
FIG. 27 shows an SEM image of an appearance in Reference Example 5.
Figure 28:
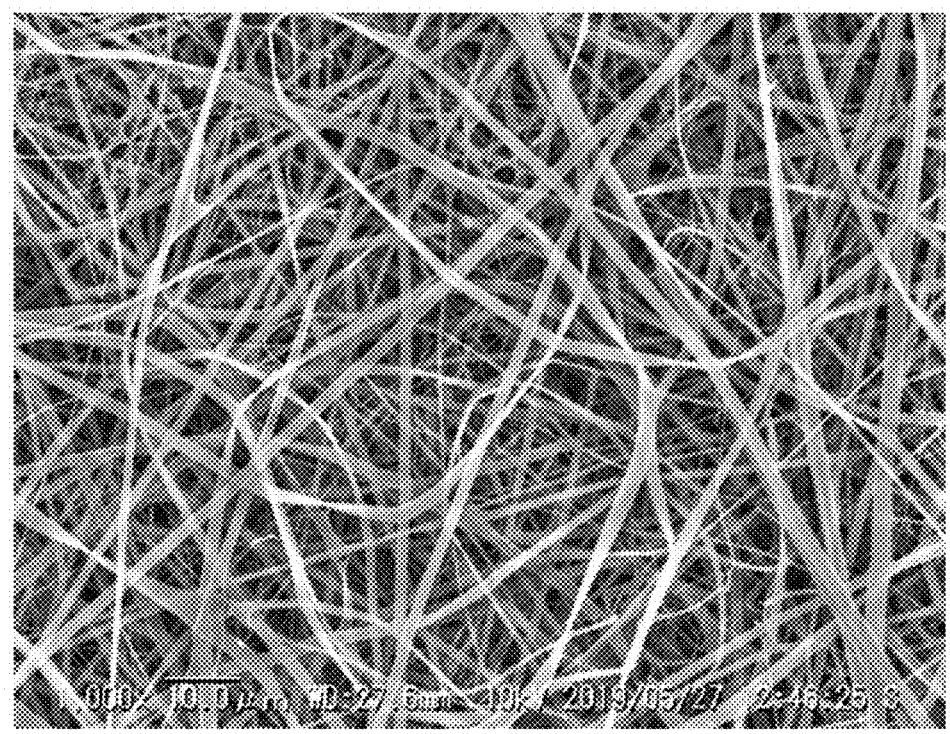
FIG. 28 shows an SEM image of an appearance in Reference Example 5.
Figure 29:
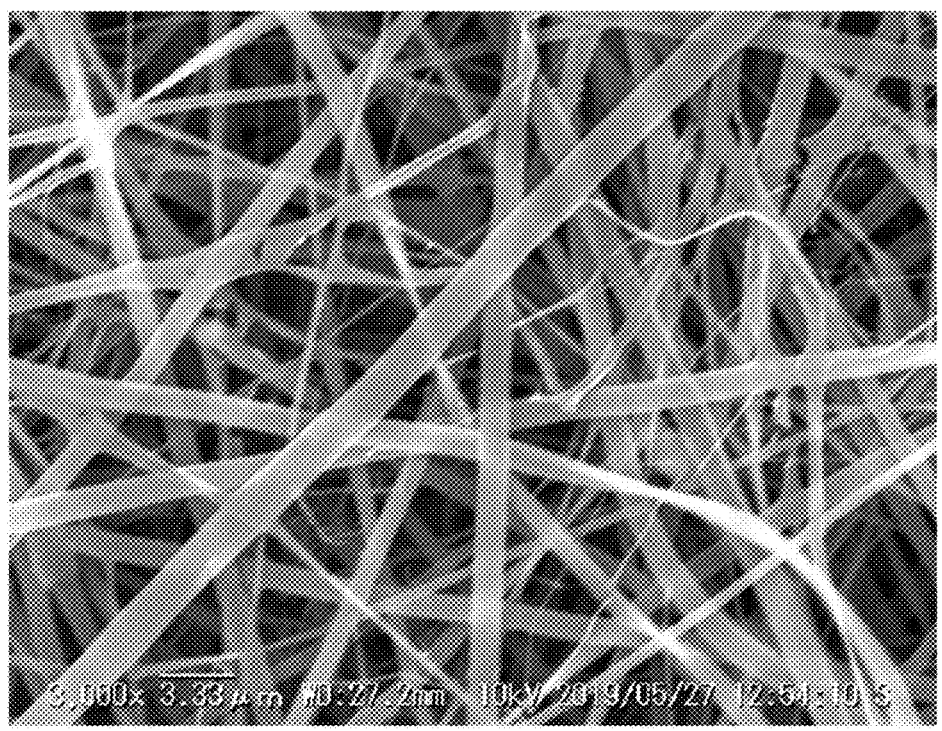
FIG. 29 shows an SEM image of an appearance in Reference Example 5.

A surface of the sheet of Reference Example 5 was observed by using a scanning electron microscope (JSM-6510, manufactured by JEOL Ltd.). An observation voltage of the scanning electron microscope was set to 10 kV. FIG. 27, FIG. 28, and FIG. 29 show SEM images of appearances in Reference Example 5. FIG. 27 shows an SEM image when observation magnification is set to 100 times. FIG. 28 shows an SEM image when observation magnification is set to 1000 times. FIG. 29 shows an SEM image when observation magnification is set to 3000 times. As shown in FIG. 27 to FIG. 29, fibers having a core-shell type of structure were deposited to produce the nonwoven fabric.

Figure 30:
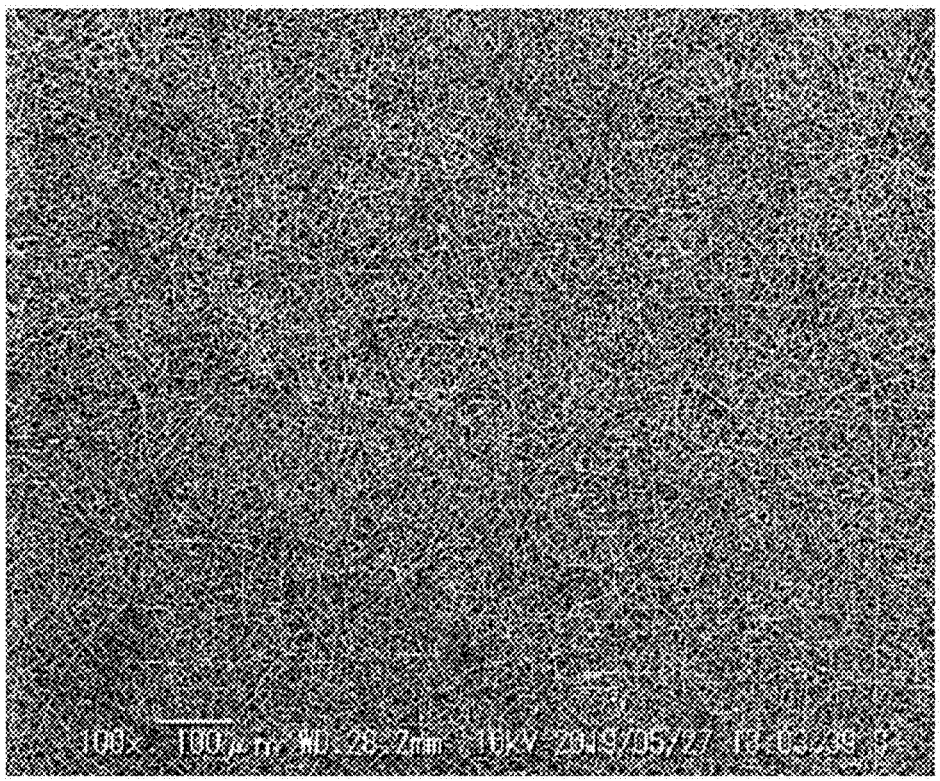
FIG. 30 shows an SEM image of an appearance in Reference Example 6.
Figure 31:
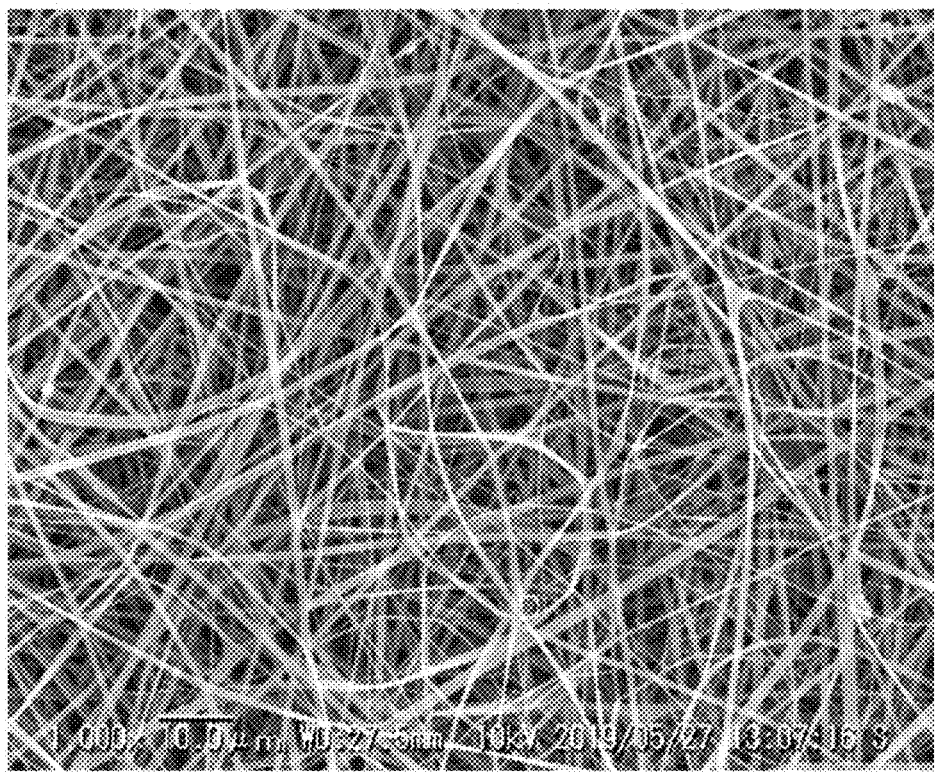
FIG. 31 shows an SEM image of an appearance in Reference Example 6.
Figure 32:
FIG. 32 shows an SEM image of an appearance in Reference Example 6.

Similarly, a surface of the sheet of Reference Example 6 was observed. FIG. 30, FIG. 31, and FIG. 32 show SEM images of appearances in Reference Example 6. FIG. 30 shows an SEM image when observation magnification is set to 100 times. FIG. 31 shows an SEM image when observation magnification is set to 1000 times. FIG. 32 shows an SEM image when observation magnification is set to 3000 times. As shown in FIG. 30 to FIG. 32, fibers having a core-shell type of structure were deposited to produce the nonwoven fabric.

Figure 33:
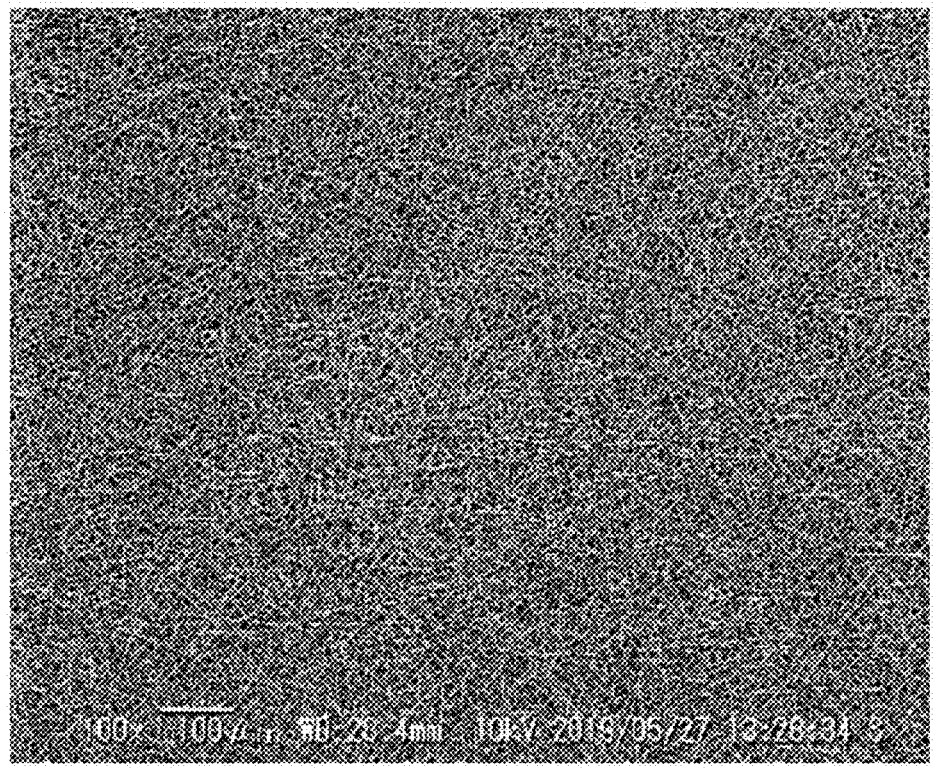
FIG. 33 shows an SEM image of an appearance in Reference Example 7.
Figure 34:
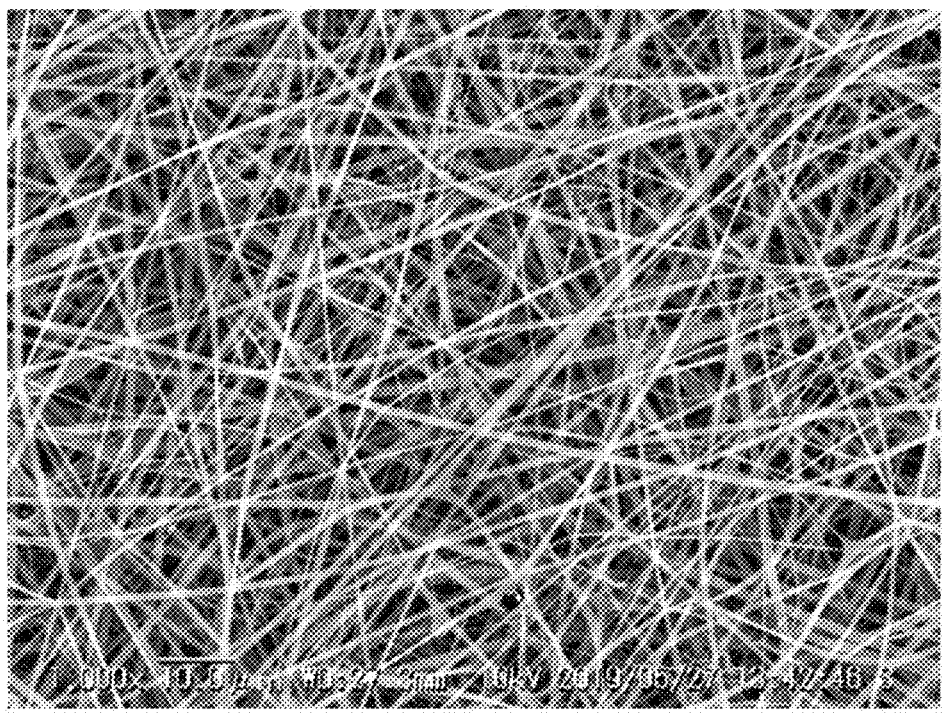
FIG. 34 shows an SEM image of an appearance in Reference Example 7.
Figure 35:
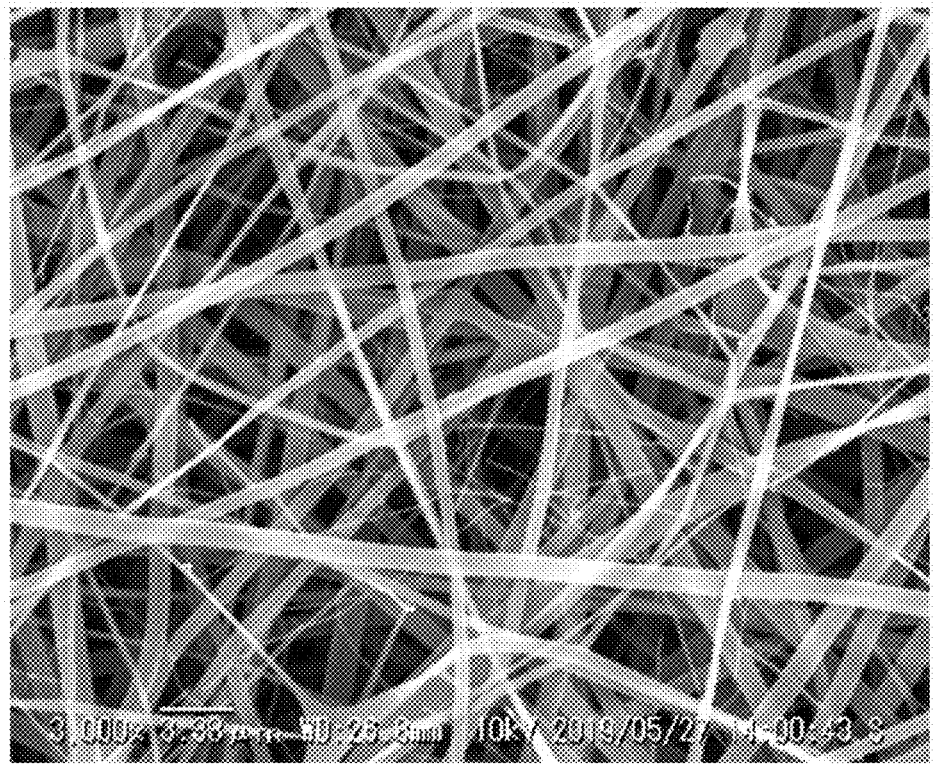
FIG. 35 shows an SEM image of an appearance in Reference Example 7.

Similarly, a surface of the sheet of Reference Example 7 was observed. FIG. 33, FIG. 34, and FIG. 35 show SEM images of appearances in Reference Example 7. FIG. 33 shows an SEM image when observation magnification is set to 100 times. FIG. 34 shows an SEM image when observation magnification is set to 1000 times. FIG. 35 shows an SEM image when observation magnification is set to 3000 times. As shown in FIG. 33 to FIG. 35, fibers having a core-shell type of structure were deposited to produce the nonwoven fabric.

Considering the results of Reference Examples 5 to 7 and the findings obtained in Example 1 and Reference Examples 1 to 4, it can be seen that during the electrospinning process, for example, by gradually increasing the discharge rate of the SF-HFIP solution and gradually decreasing the discharge rate of the collagen-HFIP solution, it is possible to produce, as the sheet of Example 1, a sheet in which the abundance ratios of SF and collagen change in the thickness direction thereof, even when atelocollagen is used as the first polymer material and silk fibroin is used as the second polymer material.

Further, as described above, collagen has high biodegradability or bioabsorbability in comparison with fibroin. Accordingly, it can be seen that it is possible to produce, as the sheet of Example 1 for example, a sheet in which the degradation or the absorption progresses from one side of the sheet into the living body, even when atelocollagen is used as the first polymer material and silk fibroin is used as the second polymer material.

While the embodiments of the present invention have been described, the technical scope of the invention is not limited to the above described embodiments. It is apparent to persons skilled in the art that various alterations and improvements can be added to the above-described embodiments. Further, within a technically consistent range, the matters described for the specific embodiment can be applied to another embodiment. It is also apparent from the scope of the claims that the embodiments added with such alterations or improvements can be included in the technical scope of the invention.

The operations, procedures, steps, and stages of each process performed by an apparatus, system, program, material and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

EXPLANATION OF REFERENCES

66: spinning jet, 68: web, 100: soft tissue repair material, 102: surface, 104: surface, 110: cross section, 120: surface layer region, 140: support layer region, 160: fiber, 162: shell portion, 164: core portion, 170: fiber, 172: shell portion, 174: core portion, 400: soft tissue repair material, 420: surface layer region, 600: electrospinning system, 610: core shell nozzle, 612: outer cylinder, 614: inner cylinder, 620: syringe, 622: pump, 640: syringe, 642: pump, 650: collector plate, 652: position adjustment unit, 660: power source, 670: control unit, 700: control pattern, 720: control pattern, 740: control pattern, 800: control pattern, 820: control pattern, 840: control pattern, 900: electrospinning system, 912: single nozzle, 914: single nozzle, 1000: electrospinning system, 1010: single nozzle, 1100: soft tissue repair material, 1102: surface, 1104: surface, 1112: surface layer region, 1114: support layer region, 1120: monolith, 1140: nonwoven fabric, 1142: sparse portion, 1144: dense portion, 1200: soft tissue repair material, 1202: inner cavity surface, 1204: outer cavity surface, 1300: sheet shaped material, 1400: cylinder shaped woven fabric, 2110: curve, 2112: curve, 2114: curve, 2120: curve, 2130: curve, 2140: curve, 2210: curve, 2220: curve, 2230: curve, 2240: curve, 2250: curve, 2600: sheet, 2620: layer, 2640: layer, 2660: layer

What is claimed is:

1. A porous body which has a first surface and a second surface, and which comprises a first polymer material and a second polymer material, wherein
a Young's modulus of the first polymer material is lower than a Young's modulus of the second polymer material,
absorbability of the first polymer material with respect to phosphate buffered saline is greater than absorbability of the second polymer material with respect to phosphate buffered saline,
a composition of the porous body in a first region and a composition of the porous body in a second region are different from each other,
a distance between the first region and the first surface is shorter than a distance between the second region and the first surface, and
the second polymer material comprises at least one selected from a group consisting of (i) chitin, sericin, fibroin, carboxymethyl cellulose, and chitosan, and (ii) salts and derivatives of these.

2. The porous body according to claim 1, wherein
the first polymer material is at least one selected from a group consisting of polyvinyl alcohol, collagen, atelocollagen, gelatin, hyaluronic acid, alginic acid, biodegradable polyurethane and polyethylene carbonate, and salts or derivatives of these, and
the second polymer material is silk fibroin, or its salts or derivatives.

3. The porous body according to claim 1,
(a) a ratio of a density of the second polymer material to a density of the first polymer material in the first region of the porous body, and (b) a ratio of a density of the second polymer material to a density of the first polymer material in the second region of the porous body are different from each other.

4. The porous body according to claim 1, comprising:
a first surface layer that is porous and is arranged on a surface of the porous body on a first surface side; and
a support layer that is porous and is arranged on a second surface side of the first surface layer to support the first surface layer, wherein
the first region is arranged on at least a part of the first surface layer, and
the second region is arranged on at least a part of the support layer.

5. The porous body according to claim 4, wherein
each of the first surface layer and the support layer has a web of a composite fiber that comprises the first polymer material and the second polymer material, and
(i) a ratio of a mass of the second polymer material to a mass of the first polymer material in the composite fiber of the first region is smaller than (ii) a ratio of a mass of the second polymer material to a mass of the first polymer material in the composite fiber of the second region.

6. The porous body according to claim 4, wherein
each of the first surface layer and the support layer has a web of a composite fiber that comprises the first polymer material and the second polymer material,
the composite fiber has a core-shell structure including a core of the second polymer material and a shell of the first polymer material, and
(i) a ratio of a diameter or equivalent diameter of the core to a diameter or equivalent diameter of the shell in the composite fiber of the first region is smaller than (ii) a ratio of a diameter or equivalent diameter of the core to a diameter or equivalent diameter of the shell in the composite fiber of the second region.

7. The porous body according to claim 4, wherein
(c) a ratio of a density of the second polymer material to a density of the first polymer material in a third region of the porous body, and (b) the ratio of the density of the second polymer material to the density of the first polymer material in the second region of the porous body are different from each other,
a distance between the third region and the first surface is shorter than the distance between the second region and the first surface, and
the third region is arranged on at least a part of the support layer.

8. The porous body according to claim 4, further comprising:
a second surface layer that is porous and is arranged on a surface of the porous body on a second surface side,
wherein the support layer is arranged between the first surface layer and the second surface layer.

9. The porous body according to claim 8, wherein
(a) a ratio of a density of the second polymer material to a density of the first polymer material in the first region of the porous body is smaller than (b) a ratio of a density of the second polymer material to a density of the first polymer material in the second region of the porous body,
(d) a ratio of a density of the second polymer material to a density of the first polymer material in a fourth region of the porous body is smaller than (b) the ratio of the density of the second polymer material to the density of the first polymer material in the second region of the porous body,
a distance between the fourth region and the first surface is longer than the distance between the second region and the first surface, and
the fourth region is arranged on at least a part of the second surface layer.

10. The porous body according to claim 1, the porous body having (i) a sheet shape or a film shape, (ii) a tube shape or a roll shape, or (iii) a block shape, a column shape, or a pad shape.

11. The porous body according to claim 1, wherein
the porous body has a tube shape,
the first surface is a inner cavity surface of the porous body, and
the second surface is outer cavity surface of the porous body.

12. A hollow material having a tube shape, comprising
a structure obtained by multiple times winding a sheet shaped material including the porous body according to claim 1.

13. A hollow material having a tube shape, comprising
a structure obtained by multiple times folding a cloth including the porous body according to claim 1.

14. An artificial blood vessel comprising the porous body according to claim 11.

15. A material for medical use which comprises the porous body according to claim 1.

16. The porous body according to claim 1, wherein
the first polymer material comprises at least one substance selected from a group consisting of a first biodegradable plastic, a first biopolymer, and a first natural polymer,
the first biodegradable plastic is at least one selected from a group consisting of (i) poly (glycolic acid), polyvinyl alcohol, polyglactin, polyethylene carbonate, and degradable polyurethane, and (ii) at least two copolymers of monomers constituting these, or a copolymer of at least one of the monomers constituting these and another monomer, and (iii) salts and derivatives of these,
the first biopolymer is at least one selected from a group consisting of (i) collagen, fibrin, alginic acid, and hyaluronic acid, and (ii) at least two copolymers of monomers constituting these, or a copolymer of at least one of the monomers constituting these and another monomer, and (iii) salts and derivatives of these, and
the first natural polymer is at least one selected from a group consisting of (i) chitosan, and (ii) at least two copolymers of monomers constituting these, or a copolymer of at least one of the monomers constituting these and another monomer, and (iii) salts and derivatives of these.

* * * * *